(12) United States Patent
Saito

(10) Patent No.: US 7,410,778 B2
(45) Date of Patent: Aug. 12, 2008

(54) ESTROGEN RECEPTOR GENES AND UTILIZATION THEREOF

(75) Inventor: Koichi Saito, Takarazuka (JP)

(73) Assignee: Sumitomo Chemical Company Limited, Tokyo (JP)

( * ) Notice: Subject to any disclaimer, the term of this patent is extended or adjusted under 35 U.S.C. 154(b) by 49 days.

(21) Appl. No.: 11/041,745

(22) Filed: Jan. 24, 2005

(65) Prior Publication Data

US 2005/0158786 A1    Jul. 21, 2005

Related U.S. Application Data

(63) Continuation of application No. PCT/JP02/07405, filed on Jul. 23, 2002.

(51) Int. Cl.
| | |
|---|---|
| C12P 21/06 | (2006.01) |
| C12P 21/04 | (2006.01) |
| C07H 21/04 | (2006.01) |
| C12N 15/00 | (2006.01) |
| C12N 5/00 | (2006.01) |
| C12N 5/06 | (2006.01) |

(52) U.S. Cl. .............. 435/69.1; 536/23.5; 536/24.1; 435/320.1; 435/325; 435/70.1; 435/70.3; 435/348

(58) Field of Classification Search ............... None
See application file for complete search history.

(56) References Cited

FOREIGN PATENT DOCUMENTS

| JP | 2001-352992 | * 12/2001 |
|---|---|---|
| JP | 2001-352992 A1 | 12/2001 |

OTHER PUBLICATIONS

Wilson et al. 2004, Environ. Sci. Technol. 38:6314-6321.*
Filby et al 2005. Biol. Reprod 73:648-662.*

* cited by examiner

*Primary Examiner*—Lorraine Spector
*Assistant Examiner*—Shulamith H Shafer
(74) *Attorney, Agent, or Firm*—Panitch Schwarze Belisario & Nadel LLP

(57) ABSTRACT

A gene coding for any of the following estrogen receptors (a) to (c): (a) an estrogen receptor comprising the amino acid sequence represented by amino acid numbers 153 to 602 in the amino acid sequence of SEQ ID NO: 1, (b) an estrogen receptor comprising the amino acid sequence of SEQ ID NO: 1, and (c) an estrogen receptor comprising an amino acid sequence exhibiting 95% or more amino acid identity to the amino acid sequence represented by amino acid numbers 153 to 602 in the amino acid sequence of SEQ ID NO: 1; and the like.

17 Claims, 5 Drawing Sheets

Concentration of Bisphenol A

Concentration of DES

SEQUENCE LISTING

```
<160> NUMBER OF SEQ ID NOS: 15

<210> SEQ ID NO 1
<211> LENGTH: 602
<212> TYPE: PRT
<213> ORGANISM: Pimephales promelas

<400> SEQUENCE: 1
```

Met Ser Gly Gly Gln Thr Ser Gly Glu Ala Ala Gly Thr Arg Gln Arg
 1               5                  10                  15

His Arg Thr Asn Leu Asn Pro Glu Arg Glu Asp Leu Glu Gly Leu Ser
            20                  25                  30

Ser Pro Pro Thr Ala His Lys Leu Ser Pro Met Tyr Pro Lys Glu Glu
        35                  40                  45

His Ser Ala Glu Gly Ile Ser Ser Ser Val Asn Tyr Leu Asp Gly Ala
    50                  55                  60

Tyr Glu Tyr Pro Asp Pro Thr Gln Thr Tyr Gly Thr Thr Ser Pro Ala
65                  70                  75                  80

Glu Pro Leu Ser Val Gly Tyr Phe Leu Ala Pro Thr Asp His His Ala
                85                  90                  95

Pro Pro Val Glu Glu His Met Gln Thr Phe Ser Gly Glu Ser Ser Ser
            100                 105                 110

Pro Leu Met Phe Ala Pro Thr Ser Pro Gln Leu Ser Pro Tyr Leu Ser
        115                 120                 125

His His Gly Gly His His Ser Thr His Gln Val Ser Tyr Tyr Leu Asp
    130                 135                 140

Thr Ser Ser Ser Thr Val Tyr Arg Ser Ser Val Val Ser Ser Gln Gln
145                 150                 155                 160

Ala Gly Val Gly Leu Cys Glu Val Leu Cys Ser Ala Thr Asp Arg Gln
                165                 170                 175

Glu Met Tyr Thr Gly Ser Arg Ala Ala Gly Gly Phe Asp Ser Glu Lys
            180                 185                 190

Glu Thr Arg Phe Cys Ala Val Cys Ser Asp Tyr Ala Ser Gly Tyr His
        195                 200                 205

Tyr Gly Val Trp Ser Cys Glu Gly Cys Lys Ala Phe Phe Lys Arg Ser

```
             210                 215                 220
Ile Gln Gly His Asn Asp Tyr Val Cys Pro Ala Thr Asn Gln Cys Thr
225                 230                 235                 240

Ile Asp Arg Asn Arg Arg Lys Ser Cys Gln Ala Cys Arg Leu Arg Lys
                245                 250                 255

Cys Tyr Glu Val Gly Met Met Lys Gly Ile Arg Lys Asp Arg Gly
            260                 265                 270

Gly Arg Ala Ile Arg Arg Glu Arg Lys Ser Asp Asn Glu Asp Arg
            275                 280                 285

Asp Lys Ser Tyr Ser Glu Gln Ser Gly Arg Val Gly Leu Arg Thr Pro
290                 295                 300

Gln Asp Lys Arg Lys Ser Ser Ala Glu Val Val Ser Ala Leu Cys
305                 310                 315                 320

Met Pro Pro Asp Gln Val Leu Val Leu Leu Gly Ala Glu Pro Pro
                325                 330                 335

Ala Val Cys Ser Arg Gln Lys His Ser Pro Pro Tyr Thr Glu Ile Thr
                340                 345                 350

Met Met Ser Leu Leu Thr Asn Met Ala Asp Lys Glu Leu Val His Met
            355                 360                 365

Ile Ala Trp Ala Lys Lys Val Pro Gly Phe Gln Asp Leu Ser Leu His
370                 375                 380

Asp Gln Val Gln Leu Leu Glu Ser Ser Trp Leu Glu Val Leu Met Ile
385                 390                 395                 400

Gly Leu Ile Trp Arg Ser Ile His Ser Pro Gly Lys Leu Ile Phe Ala
                405                 410                 415

Gln Asp Leu Ile Leu Asp Arg Asn Glu Gly Glu Cys Val Glu Gly Met
                420                 425                 430

Ala Glu Ile Phe Asp Met Leu Leu Ala Thr Val Ala Arg Leu Arg Ser
            435                 440                 445

Leu Lys Leu Lys Leu Glu Glu Phe Val Cys Leu Lys Ala Ile Ile Leu
450                 455                 460

Leu Asn Ser Gly Ala Phe Ser Phe Cys Ser Ser Pro Val Glu Pro Leu
465                 470                 475                 480

Met Asp Ser Phe Met Val Gln Cys Met Leu Asp Asn Ile Thr Asp Ala
                485                 490                 495

Leu Ile Tyr Gly Ile Ser Lys Ser Gly Ala Ser Leu Gln Leu Gln Ser
            500                 505                 510

Arg Arg Gln Ala Gln Leu Leu Leu Leu Leu Ser His Ile Arg His Met
            515                 520                 525

Ser Asn Lys Gly Met Glu His Leu Tyr His Met Lys Cys Lys Asn Arg
530                 535                 540

Val Pro Leu Tyr Asp Leu Leu Leu Glu Met Leu Asp Ala Gln Arg Phe
545                 550                 555                 560

Gln Ser Pro Gly Glu Val Gln Arg Leu Gly Ala Gln Ser Glu Lys Asp
                565                 570                 575

Pro Pro Ser Thr Pro Pro Thr Arg Gly Pro Gly Ala Met Gln Pro Asn
                580                 585                 590

Thr Gly Cys Leu Ser Gln Ser Pro Asp Pro
            595                 600

<210> SEQ ID NO 2
<211> LENGTH: 1965
<212> TYPE: DNA
<213> ORGANISM: Pimephales promelas
```

```
<220> FEATURE:
<221> NAME/KEY: CDS
<222> LOCATION: (4)...(1812)

<400> SEQUENCE: 2 gtg atg tct gga ggg cag acc agc gga gag gct gct ggt acc agg cag      48
    Met Ser Gly Gly Gln Thr Ser Gly Glu Ala Ala Gly Thr Arg Gln
    1               5                  10                  15 cga cac agg acc aac ctg aac ccg gag aga gaa gac ctg gag gga ctt      96
Arg His Arg Thr Asn Leu Asn Pro Glu Arg Glu Asp Leu Glu Gly Leu
                 20                  25                  30 tcc tca ccg ccc act gcc cac aaa ctc tcg cct atg tac ccc aag gag     144
Ser Ser Pro Pro Thr Ala His Lys Leu Ser Pro Met Tyr Pro Lys Glu
             35                  40                  45 gag cac agc gca gag ggc atc agc tcc tct gtc aat tac ctt gat gga     192
Glu His Ser Ala Glu Gly Ile Ser Ser Ser Val Asn Tyr Leu Asp Gly
         50                  55                  60 gct tat gag tac cca gac ccc aca cag acc tat ggc acc acg tca ccc     240
Ala Tyr Glu Tyr Pro Asp Pro Thr Gln Thr Tyr Gly Thr Thr Ser Pro
 65                  70                  75 gca gag cct ctc tct gtc gga tac ttc ctg gct ccc acg gac cac cac     288
Ala Glu Pro Leu Ser Val Gly Tyr Phe Leu Ala Pro Thr Asp His His
 80                  85                  90                  95 gca ccc cct gtc gaa gaa cat atg cag acg ttc agc gga gaa tcc agc     336
Ala Pro Pro Val Glu Glu His Met Gln Thr Phe Ser Gly Glu Ser Ser
                100                 105                 110 agc cct ctc atg ttt gca ccc acc agc cct cag ctg tcc ccg tac ctg     384
Ser Pro Leu Met Phe Ala Pro Thr Ser Pro Gln Leu Ser Pro Tyr Leu
            115                 120                 125 agc cat cat gga gga cac cac tcg acc cac cag gtg tcc tac tac ctg     432
Ser His His Gly Gly His His Ser Thr His Gln Val Ser Tyr Tyr Leu
        130                 135                 140 gac acc tcg tct agc aca gtc tac agg tcc agt gtg gtg tct tct cag     480
Asp Thr Ser Ser Ser Thr Val Tyr Arg Ser Ser Val Val Ser Ser Gln
145                 150                 155 cag gca ggt gtt ggt ctg tgt gag gtg ttg tgc agt gcg act gac agg     528
Gln Ala Gly Val Gly Leu Cys Glu Val Leu Cys Ser Ala Thr Asp Arg
160                 165                 170                 175 cag gag atg tac acc gga tca aga gct gca gga gga ttt gat tca gag     576
Gln Glu Met Tyr Thr Gly Ser Arg Ala Ala Gly Gly Phe Asp Ser Glu
                180                 185                 190 aag gag acg cgc ttc tgt gcg gtg tgc agt gac tat gct tcc ggc tat     624
Lys Glu Thr Arg Phe Cys Ala Val Cys Ser Asp Tyr Ala Ser Gly Tyr
            195                 200                 205 cat tat gga gtc tgg tcc tgt gag gga tgc aaa gct ttc ttc aag aga     672
His Tyr Gly Val Trp Ser Cys Glu Gly Cys Lys Ala Phe Phe Lys Arg
        210                 215                 220 agc att cag ggt cac aat gac tat gtt tgt cca gca acc aac cag tgc     720
Ser Ile Gln Gly His Asn Asp Tyr Val Cys Pro Ala Thr Asn Gln Cys
    225                 230                 235 act att gac aga aac cgc agg aag agc tgc caa gca tgc aga cta cgc     768
Thr Ile Asp Arg Asn Arg Arg Lys Ser Cys Gln Ala Cys Arg Leu Arg
240                 245                 250                 255 aag tgt tat gaa gta ggc atg atg aaa gga ggt att cgt aaa gac cgc     816
Lys Cys Tyr Glu Val Gly Met Met Lys Gly Gly Ile Arg Lys Asp Arg
                260                 265                 270 ggt ggc cgc gct atc agg cgt gag cgg agg aag agc gat aat gag gat     864
Gly Gly Arg Ala Ile Arg Arg Glu Arg Arg Lys Ser Asp Asn Glu Asp
            275                 280                 285 cgt gac aag agc tac agt gag cag tca ggc cgt gtt gga ctg agg aca     912
Arg Asp Lys Ser Tyr Ser Glu Gln Ser Gly Arg Val Gly Leu Arg Thr
```

```
                                                                           -continued Arg Asp Lys Ser Tyr Ser Glu Gln Ser Gly Arg Val Gly Leu Arg Thr
        290                 295                 300 cct cag gac aag agg aag aag agc agc gcc gag gtg gtc agt gct tta          960
Pro Gln Asp Lys Arg Lys Lys Ser Ser Ala Glu Val Val Ser Ala Leu
        305                 310                 315 tgc atg cca cct gac cag gtg ctg gtg ttg ctt ctg ggt gca gag cca         1008
Cys Met Pro Pro Asp Gln Val Leu Val Leu Leu Leu Gly Ala Glu Pro
320                 325                 330                 335 ccg gct gtc tgt tca cgt cag aag cac agc ccc ccg tac acc gag atc         1056
Pro Ala Val Cys Ser Arg Gln Lys His Ser Pro Pro Tyr Thr Glu Ile
                340                 345                 350 acc atg atg tcc ctg ctc aca aac atg gct gac aaa gaa ctc gtc cac         1104
Thr Met Met Ser Leu Leu Thr Asn Met Ala Asp Lys Glu Leu Val His
        355                 360                 365 atg atc gcc tgg gct aag aaa gta cca ggg ttc cag gac ctc tct ctg         1152
Met Ile Ala Trp Ala Lys Lys Val Pro Gly Phe Gln Asp Leu Ser Leu
        370                 375                 380 cat gac cag gtt cag ttg ttg gag agc tct tgg ctg gag gtg ttg atg         1200
His Asp Gln Val Gln Leu Leu Glu Ser Ser Trp Leu Glu Val Leu Met
        385                 390                 395 atc ggc ctc ata tgg agg tcc att cat tca cct gga aaa ctc atc ttt         1248
Ile Gly Leu Ile Trp Arg Ser Ile His Ser Pro Gly Lys Leu Ile Phe
400                 405                 410                 415 gct cag gat ctc atc ctc gat agg aat gaa gga gaa tgt gtc gag ggg         1296
Ala Gln Asp Leu Ile Leu Asp Arg Asn Glu Gly Glu Cys Val Glu Gly
                420                 425                 430 atg gct gag att ttc gac atg ctt ttg gcg act gtg gct cga tta cgg         1344
Met Ala Glu Ile Phe Asp Met Leu Leu Ala Thr Val Ala Arg Leu Arg
        435                 440                 445 agt cta aaa ctc aag ctg gag gaa ttt gta tgt ctt aaa gcc atc ata         1392
Ser Leu Lys Leu Lys Leu Glu Glu Phe Val Cys Leu Lys Ala Ile Ile
        450                 455                 460 ctt ctc aat tct ggt gca ttt tca ttc tgc tcc agt cca gtg gag ccc         1440
Leu Leu Asn Ser Gly Ala Phe Ser Phe Cys Ser Ser Pro Val Glu Pro
465                 470                 475 ctg atg gac agc ttc atg gtg cag tgc atg ctg gac aac atc act gat         1488
Leu Met Asp Ser Phe Met Val Gln Cys Met Leu Asp Asn Ile Thr Asp
480                 485                 490                 495 gcc ctc ata tac ggg atc agc aaa tcc ggt gcc tct ctg cag ctg cag         1536
Ala Leu Ile Tyr Gly Ile Ser Lys Ser Gly Ala Ser Leu Gln Leu Gln
                500                 505                 510 tcc cgg cgt cag gcg cag ctc ctg cta ctg ctc tcc cac atc aga cac         1584
Ser Arg Arg Gln Ala Gln Leu Leu Leu Leu Leu Ser His Ile Arg His
        515                 520                 525 atg agc aac aaa gga atg gag cac tta tat cat atg aaa tgt aag aat         1632
Met Ser Asn Lys Gly Met Glu His Leu Tyr His Met Lys Cys Lys Asn
        530                 535                 540 cga gtc ccg ctg tat gat ctt ttg ctg gag atg ctg gat gcc cag cga         1680
Arg Val Pro Leu Tyr Asp Leu Leu Leu Glu Met Leu Asp Ala Gln Arg
        545                 550                 555 ttc caa tcc cca gga gag gtg cag cga ctg gga gca cag agt gag aaa         1728
Phe Gln Ser Pro Gly Glu Val Gln Arg Leu Gly Ala Gln Ser Glu Lys
560                 565                 570                 575 gac ccc ccg tcc aca cca ccc acc aga gga cct gga gcc atg cag ccc         1776
Asp Pro Pro Ser Thr Pro Pro Thr Arg Gly Pro Gly Ala Met Gln Pro
                580                 585                 590 aac act ggc tgt ctc agc caa agt cca gac cca tga cctatgtacc acatac       1828
Asn Thr Gly Cys Leu Ser Gln Ser Pro Asp Pro
        595                 600
```

```
aatcccaaca gctgcagaat gtgaagactg ccaatcagga ataagaactg tgattcaaaa    1888
caacggtgga gtctctcctt gtgccttatc agagtacact ttagatttta atctagaaat    1948
taactcattt gaaaatt                                                   1965
```

<210> SEQ ID NO 3
<211> LENGTH: 408
<212> TYPE: DNA
<213> ORGANISM: Pimephales promelas

<400> SEQUENCE: 3

```
aggagcatcc aaggtcacaa tgactacgtt tgtccagcaa ccaaccagtg cactattgac      60
agaaaccgca ggaagagctg ccaagcatgc agactacgca agtgttatga agtaggcatg     120
atgaaaggag gtattcgtaa agaccgcggt ggccgcgcta tcaggcgtga gcggaggaag     180
agcgataatg aggatcgtga caagagctac agtgagcagt caggccgtgt tggactgagg     240
acacctcagg acaagaggaa gaagagcagc gccgaggtgg tcagtgcttt atgcatgcca     300
cctgaccagg tgctggtgtt gcttctgggt gcagagccac cggctgtctg ttcacgtcag     360
aagcacagcc ccccgtacac cgaggtcacc atgatgaccc tgctcacc                  408
```

<210> SEQ ID NO 4
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 4

```
gtgatgtctg gagggcagac cagcgga                                         27
```

<210> SEQ ID NO 5
<211> LENGTH: 24
<212> TYPE: DNA
<213> ORGANISM: Artificial Sequence
<220> FEATURE:
<223> OTHER INFORMATION: Designed oligonucleotide primer for PCR

<400> SEQUENCE: 5

```
ctgcagctgt tgggattgta tgtg                                            24
```

<210> SEQ ID NO 6
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 6

```
aggagcatcc aaggtcacaa tgactac                                         27
```

<210> SEQ ID NO 7
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 7

```
ggtgagcagg gtcatcatgg tgacctc                                         27
```

<210> SEQ ID NO 8
<211> LENGTH: 38

-continued

<210> SEQ ID NO 8
<211> LENGTH: 38
<212> TYPE: DNA
<213> ORGANISM: Artificial Sequence
<220> FEATURE:
<223> OTHER INFORMATION: Designed oligonucleotide primer for PCR

<400> SEQUENCE: 8
gccactagtc caccatgtct ggagggcaga ccagcgga                38

<210> SEQ ID NO 9
<211> LENGTH: 21
<212> TYPE: DNA
<213> ORGANISM: Artificial Sequence
<220> FEATURE:
<223> OTHER INFORMATION: Designed oligonucleotide primer for PCR

<400> SEQUENCE: 9
aattttcaaa tgagttaatt t                21

<210> SEQ ID NO 10
<211> LENGTH: 52
<212> TYPE: DNA
<213> ORGANISM: Artificial Sequence
<220> FEATURE:
<223> OTHER INFORMATION: Designed oligonucleotide to synthesize promoter
       DNA

<400> SEQUENCE: 10
gatctcgact ataaagaggg caggctgtcc tctaagcgtc accacgactt ca                52

<210> SEQ ID NO 11
<211> LENGTH: 52
<212> TYPE: DNA
<213> ORGANISM: Artificial Sequence
<220> FEATURE:
<223> OTHER INFORMATION: Designed oligonucleotide to synthesize promoter
       DNA

<400> SEQUENCE: 11
agcttgaagt cgtggtgacg cttagaggac agcctgccct ctttatagtc ga                52

<210> SEQ ID NO 12
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 12
gccgaattcg gcatgatgaa aggaggtatt                30

<210> SEQ ID NO 13
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 13
gccgtcgact catgggtctg gactttggct                30

<210> SEQ ID NO 14
<211> LENGTH: 33
<212> TYPE: DNA
<213> ORGANISM: Artificial Sequence
<220> FEATURE:
<223> OTHER INFORMATION: Designed oligonucleotide primer for PCR

```
<400> SEQUENCE: 14
gccgaattcg agagagctga cgggcagagc aga                33

<210> SEQ ID NO 15
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 15
gccagatctg ctcatagttg ctggcatacc act                33
```

ESTROGEN RECEPTOR GENES AND UTILIZATION THEREOF

CROSS-REFERENCE TO RELATED APPLICATION

This application is a continuation of International Application No. PCT/JP02/007405, filed Jul. 23, 2002, the disclosure of which is incorporated herein by reference.

TECHNICAL FIELD

The present invention relates to estrogen receptor genes and the utilization thereof.

BACKGROUND ART

In recent years, some environmental chemical substances have been reported to have estrogen-like activity, and for example, feminization of wild fin has been reported on some types of chemical substances (T. Colborn, D. Dumanoski and J. P. Myers, Our Stolen Future, 1996, Dutton, N.Y.). The activity of such chemical substances leads to a disturbance of hormone balance in various organisms including human and can cause disorders or diseases. Thus, the measurement of the estrogen-like activity of chemical substances has been attempted as part of a safety test for chemical substances.

Estrogen binds to the estrogen receptor in an estrogen target cell so that the receptor is activated to bind to chromosomal estrogen response element sequences. A transcription coupling factor, which recognizes the complex of the estrogen and the estrogen receptor, binds to the response element sequences to promote the expression of the genes downstream of the sequences. For the method of determining estrogen-like activity of chemical substances, therefore, there has been a need to develop an assay system for evaluating the ability of the chemical substances to regulate the estrogen receptor activity, and there has been a demand for an estrogen receptor gene which is applicable in such an assay system.

DISCLOSURE OF INVENTION

Under the circumstances, the inventor has made active investigations and succeeded in isolating an estrogen receptor gene from a fathead minnow, and aquatic animal model, to complete the present invention.

Thus, the present invention provides:

1) A gene coding for any of the following estrogen receptors (a) to (c) (hereinafter, referred to as the inventive gene):

(a) an estrogen receptor comprising the amino acid sequence represented by amino acid numbers 153 to 602 in the amino acid sequence of SEQ ID NO: 1, (b) an estrogen receptor comprising the amino acid sequence of SEQ ID NO: 1, and (c) an estrogen receptor comprising an amino acid sequence exhibiting 95% or more amino acid identity to the amino acid sequence represented by amino acid numbers 153 to 602 in the amino acid sequence of SEQ ID NO: 1;

2) An estrogen receptor gene comprising any of the following nucleotide sequences (d) to (e):

(d) the nucleotide sequence represented by nucleotide numbers 460 to 1809 in the nucleotide sequence of SEQ ID NO: 2, and (e) the nucleotide sequence represented by nucleotide numbers 4 to 1809 in the nucleotide sequence of SEQ ID NO: 2;

3) A vector comprising the inventive gene (hereinafter, referred to as the inventive vector);

4) A method for producing a vector, comprising a step of incorporating the inventive gene into a vector replicable in a host cell;

5) A transformant, wherein the inventive gene or the inventive vector is introduced into a host cell (hereinafter, referred to as the inventive transformant);

6) A method for producing a transformant, comprising a step of introducing the inventive gene or the inventive vector into a host cell;

7) A method for manufacturing an estrogen receptor, comprising a step of culturing the inventive transformant to produce estrogen receptor;

8) A DNA comprising 300 nucleotides or more of partial nucleotide sequence of the inventive gene;

9) The DNA according to the above 9, wherein said partial nucleotide sequence is a nucleotide sequence coding for a ligand binding domain of the estrogen receptor;

10) An estrogen receptor comprising any of the following amino acid sequences (f) to (h) (hereinafter, referred to as the inventive receptor):

(f) the amino acid sequence represented by amino acid numbers 153 to 602 in the amino acid sequence of SEQ ID NO: 1, (g) the amino acid sequence of SEQ ID NO: 1, and (h) an amino acid sequence exhibiting 95% or more amino acid identity to the amino acid sequence represented by amino acid numbers 153 to 602 in the amino acid sequence of SEQ ID NO: 1;

11) A method for evaluating the ability of a test substance to regulate estrogen receptor activity, comprising a step of:

bringing the test substance into contact with a transformant, wherein a reporter gene linked downstream of a transcriptional control region including an estrogen response element sequence, and the inventive gene are introduced into a host cell, and measureing an expression amount of said reporter gene in said transformant;

12) Use of the inventive gene for measuring the ability of a test substance to regulate estrogen receptor activity in a two-hybrid system, wherein in said system, ligand-dependent formation of a complex comprising:

an estrogen receptor and a transcription coupling factor capable of ligand-dependently binding to the estrogen receptor, or a receptor binding domain of said transcription coupling factor;

results in activation of transcription of a reporter gene;

13) Use of the DNA according the above 8 for measuring the ability of a test substance to regulate estrogen receptor activity in a two-hybrid system, wherein in said system, ligand-dependent formation of a complex comprising:

an estrogen receptor and a transcription coupling factor capable of ligand-dependently binding to the estrogen receptor, or receptor binding domain of said transcription coupling factor;

results in activation of transcription of a reporter gene; and

14) A receptor binding assay comprising a step of bringing a test substance into contact with the inventive receptor and incubating.

BEST MODE FOR CARRYING OUT THE INVENTION

Figure 1:
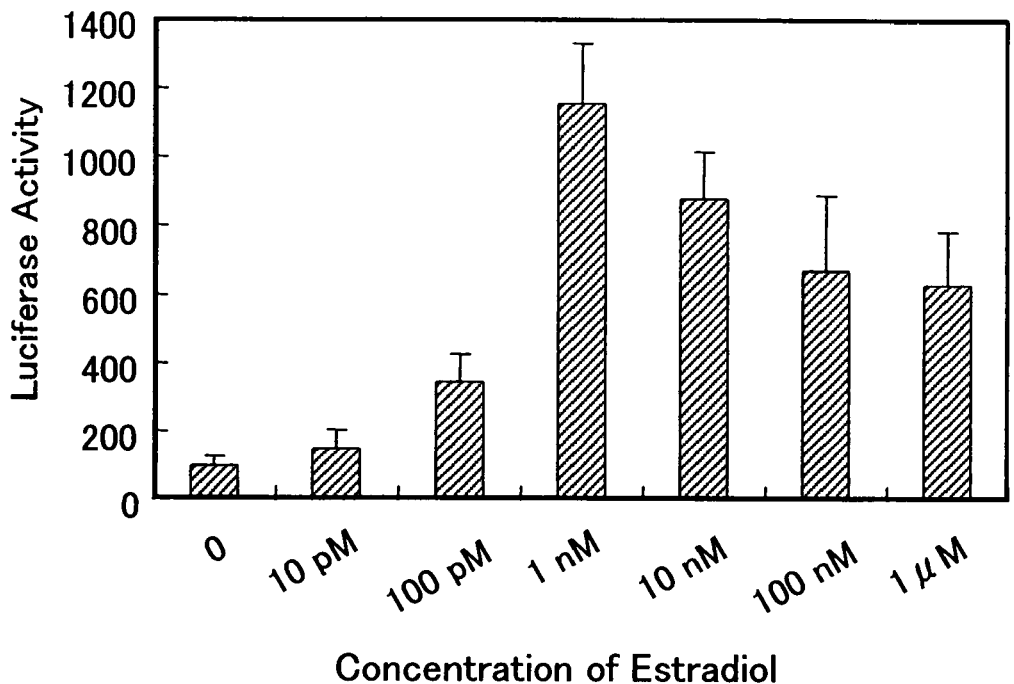
FIG. 1 is a diagram showing a result of measuring the ability of E2 to activate the estrogen receptor activity by the reporter assay using the inventive gene. The abscissa axis represents the concentration of estradiol in each experimental section. The left end column indicated by O corresponds to an experimental section in which DMSO was added at a final concentration of 0.1% in place of the DMSO solution of E2 (E2-free section). The ordinate axis represents the luciferase activity value, where the luciferase activity value of the E2-free section is normalized as 100.

The present invention is described in detail below.

The inventive gene includes a gene coding an estrogen receptor comprising the amino acid sequence represented by amino acid numbers 153 to 602 in the amino acid sequence of SEQ ID NO: 1, a gene coding an estrogen receptor comprising the amino acid sequence of SEQ ID NO: 1, and a gene coding an estrogen receptor comprising an amino acid sequence exhibiting 95% or more amino acid identity to the amino acid sequence represented by amino acid numbers 153 to 602 in the amino acid sequence of SEQ ID NO: 1. Specifically, the inventive gene includes an estrogen receptor gene comprising the nucleotide sequence represented by nucleotide numbers 460 to 1809 in the nucleotide sequence of SEQ ID NO: 2, an estrogen receptor gene comprising the nucleotide sequence represented by nucleotide numbers 4 to 1809 in the nucleotide sequence of SEQ ID NO: 2, and the like.

The inventive receptor includes an estrogen receptor comprising the amino acid sequence represented by amino acid numbers 153 to 602 in the amino acid sequence of SEQ ID NO: 1, an estrogen receptor comprising the amino acid sequence of SEQ ID NO: 1, and an estrogen receptor comprising an amino acid sequence exhibiting 95% or more amino acid identity to the amino acid sequence represented by amino acid numbers 153 to 602 in the amino acid sequence of SEQ ID NO: 1.

With respect to the present invention, "an estrogen receptor comprising an amino acid sequence exhibiting 95% or more amino acid identity to the amino acid sequence represented by amino acid numbers 153 to 602 in the amino acid sequence of SEQ ID NO: 1" includes, for example, a protein comprising an amino acid sequence exhibiting 95% or more amino acid identity to the amino acid sequence represented by amino acid numbers 153 to 602 in the amino acid sequence of SEQ ID NO: 1 and having the receptor function substantially comparable to that of the estrogen receptor comprising the amino acid sequence of SEQ ID NO: 1. The receptor function can be evaluated using, for example, the reporter assay, two-hybrid system, or the receptor binding assay, all of which are described later. The difference from the amino acid sequence represented by amino acid numbers 153 to 602 in the amino acid sequence of SEQ ID NO: 1 observed in the amino acid sequence of the estrogen receptor may for example be a variation such as deletion, substitution, modification and addition of amino acids. Such a variation includes a variation which can artificially be introduced by means of a site-directed mutagenesis method or a mutagenic treatment as well as a polymorphic variation which occurs naturally such as a difference in an amino acid sequence resulting from the difference by the animal line, individual, organ and tissue.

For example, the inventive gene may be obtained from the tissue of an animal such as a fin including a fathead minnow (scientific name: *Pimephales promelas*) according to such a genetic engineering process as disclosed in the text (J. Sambrook, E. F. Frisch, and T. Maniatis, Molecular Cloning 2nd edition, Cold Spring Harbor Laboratory, 1989).

For example, first, total RNA is prepared from the tissue of a fathead minnow. Specifically, the tissue of a fathead minnow such as a liver tissue is homogenized in a solution containing a protein denaturant such as guanidine hydrochloride and guanidine thiocyanate, and then phenol, chloroform or the like is added to the homogenate to denature the proteins. The denatured proteins are removed by centrifugation or the like as a precipitated fraction, and then the recovered supernatant fraction is extracted using a guanidine hydrochloride/phenol process, a SDS-phenol process, a guanidine thiocyanate/CsCl process, or the like to give total RNA. These processes may be performed using a commercially available kit, for example, including ISOGEN (Nippon Gene).

The resultant total RNA is used as a template and an oligo dT primer is annealed to a poly A sequence of the RNA, whereby synthesizing a single-stranded cDNA using a reverse transcriptase. Then, the synthesized single-stranded cDNA is used as a template together with a primer which is an RNA obtained by inserting a nick and a gap into the RNA chain using an *E. coli* RnaseH, whereby synthesizing a double-stranded cDNA using an *E. coli* DNA polymerase I. Subsequently, the both ends of the synthesized double-stranded cDNA is made blunt using a T4 DNA polymerase. The resultant double-stranded cDNA is purified and recovered by means of a standard procedure such as a phenol-chloroform extraction and ethanol precipitation. A commercially available kit based on the methods described above may for example be a cDNA synthesis system plus (Amarsham Pharmacia Biotech) or a TimeSaver cDNA synthesis kit (Amarsham Pharmacia Biotech). Then the resulting double-stranded cDNA is ligated to a vector such as a plasmid pUC118 or phage λgt10 using a ligase to prepare a cDNA library. From a cDNA library obtained as described above, the inventive gene can be obtained for example by hybridization methods where a DNA comprising a partial nucleotide sequence of the nucleotide sequence of one of SEQ ID NO: 2 may be used as a probe, or polymerase chain reaction (hereinafter referred to as PCR) method where oligonucleotides comprising a partial nucleotide sequence of the nucleotide sequence of one of SEQ ID NO: 2 may be used as a primer.

Probes used for the hybridization method may include, for example, DNA comprising the nucleotide sequence represented by the nucleotides 4 to 129, 474 to 574, 697 to 1053, or 1726 to 1782 of SEQ ID NO:2. The hybridization may be performed under the following conditions: for example, in the presence of 6×SSC (0.9 M NaCl and 0.09 M sodium citrate), 5× Denhardt's solution (0.1% (w/v) Ficoll 400, 0.1% (w/v) polyvinylpyrrolidone, and 0.1% (w/v) BSA), 0.5% (w/v) SDS, and 100 µg/ml of denatured salmon sperm DNA or in a DIG EASY Hyb solution (Boehringer Mannheim) containing 100 µg/ml of denatured salmon sperm DNA, holding at 65° C., then in the presence of 1×SSC (0.15 M NaCl and 0.015 M sodium citrate) and 0.5% (w/v) SDS, holding at room temperature for 15 minutes twice, and in the presence of 0.1×SSC (0.015 M NaCl and 0.0015 M sodium citrate) and 0.5% (w/v) SDS, holding at 68° C. for 30 minutes.

A primer used for the PCR method may include, for example, an oligonucleotide having a length of about 20 nucleotides to about 40 nucleotides which is an oligonucleotide comprising a nucleotide sequence selected from a 5' end region of the nucleotide sequence of SEQ ID NO: 2 and which is an oligonucleotide comprising the nucleotide sequence complementary to a nucleotide sequence selected from a 3 non-translation region of the nucleotide sequence of SEQ ID No: 2. Typically, the forward primer may for example be an oligonucleotide comprising the nucleotide sequence represented by nucleotide numbers 4 to 27 in the nucleotide sequence of SEQ ID NO: 2, more specifically, an oligonucleotide consisting of the nucleotide sequence of SEQ ID NO: 4 and an oligonucleotide consisting of the nucleotide sequence of SEQ ID NO: 8. The reverse primer may for example be an oligonucleotide comprising the nucleotide sequence complementary to the nucleotide sequence represented by nucleotide numbers 1945 to 1965 in the nucleotide sequence of SEQ ID NO: 2, more specifically, an oligonucleotide consisting of the nucleotide sequence of SEQ ID NO: 9 and an oligonucleotide consisting of the nucleotide sequence of SEQ ID NO: 5. For example, PCR may be performed under the following conditions: 50 µl of a reaction solution containing 5 µl of 10× Ex Taq buffer (Takara), 4 µl of 2.5 mM DNTP mixture (wherein the mixture contains DATP, dGTP, dCTP, and dTTP at each content of 2.5 mM, and each of them is at a final concentration of 0.2 mM), 0.25 to 1.25 µl of 20 µM each primer (at each final concentration of 0.1 to 0.5 µM), 0.1 to 0.5 µg of cDNA template, and 1.25 units of ExTaq polymerase (Takara); and 30 cycles of temperature maintenance is performed, each cycle being 94° C. for 1 minute, then 55° C. for 2 minutes, and 72° C. for 2.5 minutes.

The resulting inventive gene may be cloned into a vector according to such a genetic engineering process as disclosed in the text (J. Sambrook, E. F. Frisch, and T. Maniatis, Molecular Cloning 2nd edition, Cold Spring Harbor Laboratory, 1989). Specifically, for example, the cloning may be performed using a commercially available plasmid vector such as TA cloning kit (Invitrogen) or pBluescriptII (Stratagene).

Alternatively, for example, based on the nucleotide sequence of SEQ ID NO:2, the inventive gene may be chemically synthesized by a conventional method such as a phosphite triester method (Hunkapiller, M. et al., Nature, 310, 105, 1984).

The nucleotide sequence of the resulting inventive gene may be confirmed by the Maxam-Gilbert method (for example, as disclosed in Maxam, A. M. & W. Gilbert, Proc. Natl. Acad. Sci. USA, 74, 560, 1977) or the Sanger method (for example, as disclosed in Sanger, F. & A. R. Coulson, J. Mol. Biol., 94, 441, 1975 or Sanger, F, & Nicklen and A. R. Coulson., Proc. Natl. Acad. Sci. USA, 74, 5463, 1977).

The inventive gene may be inserted into a vector operable in a host cell to which the gene is incorporated (hereinafter referred to as the basic vector) according to a conventional genetic engineering process to form the inventive vector. For example, the basic vector contains genetic information replicable in the host cell, is autonomously replicable, can be isolated or purified from the host cell, and has a detectable marker.

Examples of the basic vector applicable in constructing the inventive vector include: plasmid pUC119 (Takara) and phagemid pBluescriptII (Stratagene) each for an *E. coli* host cell; plasmids pGBT9, pGAD424, and pACT2 (Clontech) each for a budding yeast host cell; a plasmid such as pRc/RSV and pRc/CMV (Invitrogen), a virus-derived autonomous replication origin-containing vector such as bovine papilloma virus plasmid pBPV (Amersham Pharmacia Biotech) and EB virus plasmid pCEP4 (Invitrogen), and a virus such as vaccinia virus each for a mammal host cell; and an insect virus such as baculovirus for an insect host cell. When the autonomous replication origin-containing vector such as the plasmid pACT2 for the yeast, the bovine papilloma virus plasmid pBPV, and the EB virus plasmid pCEP4 is used to construct the inventive vector, the vector introduced into the host cell is held in the form of an episome in the cell.

In order to incorporate the inventive gene into baculovirus or vaccinia virus, a transfer vector may be used, which contains a nucleotide sequence homologous to the virus genome to be used. Examples of such a transfer vector include plasmids such as pVL1392 and pVL1393 (Smith, G. E., Summers M. D. et al., Mol. Cell. Biol., 3, 2156-2165, 1983) commercially available from Pharmingen, and pSFB5 (Funahashi, S. et al., J. Virol., 65, 5584-5588, 1991). When the inventive gene is introduced into the transfer vector and the vector and the virus genome are simultaneously introduced into a host cell, homologous recombination occurs between the vector and the virus genome so as to form a virus having the inventive gene incorporated in the genome. The virus genome may be a baculovirus, adenovirus, or vacciniavirus genome.

More specifically, in the process of incorporating the inventive gene into baculovirus, first, the inventive gene is inserted into a multicloning site of the transfer vector such as pVL1393 and pVL1392, and then the transfer vector DNA and Baculovirus genome DNA (Baculogold (Pharmingen)) are introduced into an insect cell line Sf21 (available from ATCC) by calcium phosphate method. The resulting cells are cultured, and then the culture is subjected to centrifugation and other processes so that viral particles are recovered, whose genome contains the inventive gene. The recovered viral particles are deproteinized with phenol or the like to give the inventive gene-containing virus genome. The resulting virus genome may be introduced into a host cell having the ability to form viral particles, such as insect cell line Sf21, by calcium phosphate method or the like. The resulting cells may be cultured so that the inventive gene-containing viral particles can be multiplied.

Alternatively, the inventive gene may be directly incorporated into a relatively small genome such as a mouse leukemia virus genome without using the transfer vector. For example, the inventive gene is incorporated into a cloning site of virus vector-DC(X) (Eli Gilboa et al., BioTechniques, 4, 504-512, 1986). The resulting inventive gene-containing virus vector may be introduced into a packaging cell such as Ampli-GPE (J. Virol., 66, 3755, 1992) to form viral particles which bear the inventive gene-containing virus genome.

A promoter operable in the host cell may be operably linked upstream of the inventive gene and incorporated into the basic vector to construct the inventive vector, which is capable of expressing the inventive gene in the host cell. The term "operably linked" means that the promoter is linked to the inventive gene in such a manner that the inventive gene can be expressed under the control of the promoter in the inventive gene-containing host cell. Examples of the promoter operable in the host cell include DNAs that exhibit a promoter activity in the host cell. Such examples include: a lactose operon promoter (lacP), a tryptophan operon promoter (trpP), an arginine operon promoter (argP), a galactose operon promoter (galP), tac promoter, T7 promoter, T3 promoter, and a λ-phage promoter (λ-pL and λ-pR) each for an *E. coli* host cell; a Rous sarcoma virus (RSV) promoter, a cytomegalovirus (CMV) promoter, a early or late simian virus (SV40) promoter, and a mouse papilloma virus (MMTV) promoter each for an animal or fission yeast host cell; and ADH1 promoter for a budding yeast host cell.

The basic vector may preliminarily contain the promoter operable in the host cell. When such a basic vector is used, the inventive gene may be inserted downstream of the promoter contained in the vector so as to be operably linked to the promoter. For example, the above plasmids pRc/RSV, pRc/CMV and the like have a cloning site downstream from the promoter operable in an animal cell. The inventive gene may be inserted into the cloning site to form a vector, which may be introduced into the animal cell to express the inventive gene. These plasmids preliminarily contain an SV40 autonomous replication origin (ori). Therefore, any of these plasmids may be introduced into a cultured cell transformed with an ori-deleted SV40 genome, such as a COS cell, so that large numbers of the plasmid can be copied in the cell, and thereby, the inventive gene incorporated in the plasmid can be expressed in a large amount. The above plasmid pACT2 for the yeast has the ADH1 promoter. Therefore, the inventive gene may be inserted downstream of the ADH1 promoter in the plasmid or a derivative thereof to form the inventive vector capable of expressing a large amount of the inventive gene in the budding yeast such as CG1945 (Clontech).

The constructed inventive vector may be introduced into the host cell to form the inventive transformant. Any conventional introducing process may be used depending on the host cell. For the introduction into an *E. coli* host cell, any conventional method may be used, for example, including calcium chloride method and electroporation method as disclosed in the text (J. Sambrook et al., Molecular Cloning 2nd edition, Cold Spring Harbor Laboratory Press, 1989). The introduction of the vector into a mammal host cell, a fin host cell or an insect host cell may be performed according to any general gene transfection method such as calcium phosphate method, DEAE dextran method, electroporation method, and lipofection method. For the introduction into an yeast host cell, for example, Yeast transformation kit (Clontech) may be used based on lithium method.

The introduction of the viral genome into the host cell via the viral vector can be made not only by any of the above general gene transfection methods but also by infecting the host cell with viral particles which carry the inventive gene-containing viral genome.

In order to select the inventive transformant, for example, a marker gene may be introduced into the host cell together with the inventive vector, and then the host cell may be cultured by any method depending on the characteristic of the marker gene. For example, the marker gene may be a drug resistance gene against a selection drug that has killing activity on the host cell, and the inventive vector-containing host cell may be cultured in a medium that contains the selection drug. Examples of the combination of the drug resistance gene and the selection drug include the combinations of a neomycin resistance gene and neomycin, a hygromycin resistance gene and hygromycin, and a blasticidin S resistance gene and blasticidin S. Alternatively, the marker gene may complement auxotrophy of the host cell, and the inventive gene-containing cell may be cultured in a minimal medium free of the nutrient concerning the auxotrophy. When the inventive vector capable of expressing the inventive gene is introduced into a host cell, the inventive transformant by be selected by using a detection method based on the estrogen binding activity.

For example, the inventive transformant in which the inventive gene is located in the chromosome of the host cell is obtained as follows. The inventive vector and the marker gene-containing vector are each digested with a restriction enzyme or the like into a linear form and then introduced into the host cell by any method as described above. The cell is cultured generally for several weeks and then selected based on the expression amount of the introduced marker gene to give a desired transformant. For example, the inventive vector which contains the drug resistance gene as the marker gene is introduced into the host cell by any method as described above. The cell is subcultured in a selection drug-containing medium for at least several weeks, and then the drug-resistant clone surviving in the form of a colony is subjected to culture for clone purification, resulting in the inventive transformant in which the inventive gene is incorporated in the chromosome of the host cell. In order to confirm the incorporation of the inventive gene in the host cell chromosome, the genome DNA may be prepared from the cell by a conventional genetic engineering method, and then the inventive gene may be detected in the prepared genome DNA by PCR, Southern hybridization, or the like using a DNA comprising a partial nucleotide sequence of the introduced inventive gene as a primer or a probe. The transformant can be stored in a frozen state and then allowed to activate as needed. Therefore, not every experiment needs the transformant preparation, and tests can be performed using the transformant with the characteristics and the handling conditions checked in advance.

The resulting inventive transformant may be cultured to produce the estrogen receptor.

For example, the inventive transformant is a microorganism, and in such a case, the transformant may be cultured using any medium that appropriately contains any carbon source, any nitrogen source, any organic or inorganic salt, and the like each for general microorganism culture. The cultivation may be carried out according to any conventional method for general microorganisms, such as solid culture method and liquid culture method (such as rotary shaking culture, reciprocal shaking culture, jar fermenter culture, and tank culture). The culture temperature and the pH of the medium can be each selected from a certain range in which the microorganism can grow. For example, the culture is generally performed at a temperature of about 15° C. to about 40° C. at a pH of about 6 to about 8. The culture time period depends on various culture conditions but is generally from about one day to about five days. When the expression vector contains an inducible promoter such as a temperature-inducible promoter and an IPTG-inducible promoter, the induction time is preferably within one day and generally several hours.

On the other hand, the transformant may be an animal cell such as a mammal cell, a fin cell and an insect cell, and the transformant may be cultured using any medium for general cell culture. If the transformant is prepared using the selection drug, the culture is preferably performed in the presence of the selection drug. For example, the mammal cell may be cultured using a DMEM medium (Nissui) containing FBS at a final content of 10% at 37° C. under 5% $CO_2$ while the medium may be replaced with fresh one every several days. After the cells are grown in a confluent state, for example, an about 0.25% (w/v) trypsin-containing PBS solution is added so that the cells are separated and dispersed. The cells are then diluted several times and inoculated into a new plate and further cultured. Similarly, the insect cell may be cultured using any insect cell culture medium such as a 10% (v/v) FBS and 2% (w/v) Yeastlate-containig Grace's medium at a culture temperature of 25° C. to 35° C. If the cell tends to peel off the plate as in the case of Sf21 cell, the cells may be dispersed by pipetting and subcultured without using the trypsin solution. When the transformant contains the virus vector such as baculovirus, the culture is preferably terminated before the cell is killed and the cytoplasmic effect is observed, for example, up to 72 hours after the viral infection.

The inventive receptor produced by the inventive transformant may be recovered from the culture by any appropriate combination of conventional isolation or purification processes. For example, after the culture is completed, the transformant cells are collected by centrifugation or the like, and the collected cells are suspended in a general buffer such as a buffer comprising 20 mM HEPES pH7, 1 mM EDTA, 1 mM DTT, and 0.5 mM PMSF and then homogenized in a Polytron, an ultrasonic apparatus, a Dounce homogenizer, or the like. The resulting homogenate may be ultracentrifuged at several tens thousand×g for several tens minutes to about one hour, and then the supernatant fraction may be taken to give the inventive receptor-containing fraction. In addition, the supernatant fraction may be subjected to any type of chromatography such as ion exchange, hydrophobic, gel filtration, or affinity chromatography to give the estrogen receptor in a further purified state. In this process, the inventive receptor-containing fraction may be identified by a DNA binding assay or the like using a probe of an oligonucleotide with a length of about 15 bp to about 200 bp including an estrogen response element sequence, a nucleotide sequence to which the estrogen receptor is capable of binding.

The resulting inventive receptor may be used in a receptor binding assay or the like for evaluating the ability or the amount of any test substance to bind to or bound to the estrogen receptor.

The inventive gene may be used in a reporter assay for evaluating the ability of any test substance to regulate the estrogen receptor activity. The ability to regulate the estrogen receptor activity may include an agonistic activity and an antagonistic activity on the estrogen receptor.

The "reporter gene linked downstream of a transcriptional control region including an estrogen response element sequence", used in the reporter assay utilizing the inventive gene, may include specifically a reporter gene linked downstream of a transcriptional control region or the like of the *Xenopus Vitellogenin* gene including the estrogen response element sequence or a reporter gene linked downstream of a transcriptional control region that includes a consensus sequence (5'-AGGTCAnnnTGACCTT-3' wherein n represents A, G, C, or T) of the estrogen response element sequence and a nucleotide sequence necessary for transcription initiation. Such a repoter gene may be used for monitoring the ability of the estrogen receptor to control transcription in the host cell. The reporter gene may be a luciferase gene, a secretory alkaline phosphatase gene, a β-galactosidase gene, a chloramphenicol acetyltransferase gene, a growth hormone gene, or the like. A preferred reporter gene is a gene coding for a reporter protein with relatively higher stability in the host cell.

The inventive gene and the reporter gene linked downstream of the transcriptional control region including the estrogen response element sequence are introduced into, for example, an estrogen receptor-absent host cell, such as HeLa, CV-1, Hepal, NIH3T3, HepG2, COS1, BF-2, and CHH-1 cells, to form a transformant. As described above, the inventive gene may be operably linked to the promoter operable in the host cell and incorporated in the basic vector before introduced into the host cell. The reporter gene linked downstream of the transcriptional control region including the estrogen response element sequence may also incorporated in the basic vector before use. For example, both of the reporter gene-containing vector in which the reporter gene is linked downstream of the transcriptional control region including the estrogen response element sequence and the inventive gene-containing vector in which the inventive gene is operably linked to the promoter operable in the host cell are introduced into the host cell together with the marker gene-containing vector. After the cell is cultured generally for several weeks, the desired transformant is selected based on the expression amount of the introduced marker gene. In the resulting transformant, the reporter gene linked downstream of the transcriptional control region including the estrogen response element sequence and the inventive gene operably linked to the operable promoter are incorporated in the host cell chromosome. In order to confirm the incorporation of the inventive gene in the host cell chromosome, the genome DNA may be prepared from the cell by a conventional genetic engineering method, and then the inventive gene may be detected in the prepared genome DNA by PCR, Southern hybridization, or the like using a DNA comprising a partial nucleotide sequence of the introduced inventive gene as a primer or a probe. The transformant can be stored in a frozen state and then allowed to activate as needed. Therefore, once the transformant is obtained, transformant preparation containing a step of introducing those genes into a host cell does not have to be made at every experiment, and the characteristics of the transformant can be maintained constant. The transformant will therefore be useful in a large scale screening with an automatic robot.

The resulting transformant is cultured in a test substance-containing medium for one day to several days to bring into contact with the test substance. A measurement is then made on the expression amount of the reporter gene of the transformant. If a substance with an estrogen-like activity in the test substance binds to the estrogen receptor produced by the transformant and activates it, the transcription of the reporter gene will be promoted so that the reporter protein encoded by the reporter gene can be stored in the transformant cell or secreted into the medium. The amount of the reporter protein is determined so that the expression amount of the reporter gene can be determined per transformant cell. For example, a luciferase reporter gene is used, and luciferin, the substrate of the luciferase, is added to a crude cell extract prepared from the transformant that has been in contact with the test substance, so that luminescence can be observed in an intensity proportional to the amount of the luciferase in the crude cell extract. Therefore, the intensity of the luminescence may be measured using a measuring apparatus such as a luminometer so that the amount of the luciferase and therefore the expression amount of the luciferase gene can be determined. In a similar manner, under the condition that the transformant is not in contact with the test substance, a measurement is made on the expression amount of the reporter gene The measured expression amount is compared with the amount measured under the test substance contact condition, so that the agonistic activity on the estrogen receptor, i.e., the ability to activate the estrogen receptor of a subsntance with an estrogen-like activity in the test substance can be evaluated. On the other hand, for example, under each of the condition that the transformant is in contact with the estrogen such as 17β-estradiol (hereinafter referred to as E2) and the condition that the transformant is in contact with the estrogen and the test substance at the same time, a measurement is made on the expression amount of the reporter gene in a similar manner to the above. The measurements under both conditions are compared with each other. If the expression amount under the latter condition is lower than that under the former condition, the test material can be evaluated as having the antagonistic activity on the estrogen receptor, i.e., the anti-activation ability on the estrogen receptor.

Based on the expression amount of the intracellular reporter gene, the inventive gene or a DNA including a partial nucleotide sequence of the inventive gene may be applied to an assay system for detecting the ability to form a complex of two types of fusion proteins (two-hybrid) and the ability of the complex to regulate the transcription (two hybrid system, Nishikawa et al., Toxicol. Appl. Pharmacol., 154, 76-83, 1999). Specifically, for example, in the two-hybrid system, where ligand-dependent formation of a complex comprising:

an estrogen receptor encoded by the inventive gene or the ligand binding domain of said estrogen receptor, and a transcription coupling factor capable of ligand-dependently binding to the estrogen receptor;

results in activation of transcription of a reporter gene, the ability of a test substance to regulate estrogen receptor activity can be evaluated by measuring any variation (increase and decrease) in the expression amount of reporter gene when the test substance is added. The ability to regulate estrogen receptor activity may include an agonist activity and an antagonist activity on the estrogen receptor.

The two-hybrid system includes, for example, the transformant, in which one each of the genes (i) to (k) listed below are incorporated together into the same host cell.

(i) A chimera gene in which a nucleotide sequence encoding a fusion protein of the DNA binding domain of the transcription control factor operable in the host cell and the inventive receptor or the ligand binding domain of said receptor is linked downstream of a promoter operable in the host cell.

(j) A chimera gene in which a nucleotide sequence encoding a fusion protein of the transcription activating domain of the transcription control factor operable in the host cell and the transcription coupling factor capable of ligand-dependently binding to the inventive receptor or the receptor binding domain of said transcription coupling factor is linked downstream of a promoter operable in the host cell.

(k) The reporter gene in which a nucleotide sequence encoding a repoter protein is linked downstream of a nucleotide sequence to which the DNA binding domain described in (i) is capable of binding and a promoter capable of being activated by the transcription activating domain described in (j).

Examples of the host cell include mammal cells, such as budding yeast cells and HeLa cells. To measure the ability of a test substance to regulate the activity of the estrogen receptor in the present invention at a higher accuracy, it is preferable to use the cells containing no intrinsic estrogen receptor.

The "DNA binding domain of the transcription control factor operable in the host cell" described in the above (i) includes, for example, the DNA binding domain of a yeast-derived transcription control factor GAL4 and bacterium-derived repressor LexA if the budding yeast cell is used as the host cell. By linking in frame the DNA encoding each of them, and the DNA of the inventive gene or the DNA comprising the partial nucleotide sequence of the inventive gene encoding the ligand binding domain of the estrogen receptor, the DNA comprising "a nucleotide sequence encoding a fusion protein of the DNA binding domain of the transcription control factor operable in the host cell and the inventive receptor or the ligand binding domain of said receptor" can be obtained. The above-mentioned "DNA comprising the partial nucleotide sequence of the inventive gene encoding the ligand binding domain of the estrogen receptor" includes, for example, the DNAs comprising the inventive gene-derived nucleotide sequences, containing the nucleotide sequence encoding the ligand binding domain of the estrogen receptor and not containing the nucleotide sequence encoding the DNA binding domain. Specifically, it includes, for example, the nucleotide sequences containing at least the nucleotide sequence represented by nucleotide numbers 852 to 1638 and not containing nucleotide sequence represented by nucleotide numbers 1 to 783 of SEQ ID NO: 2, and more specifically, includes the DNAs comprising the nucleotide sequence represented by nucleotide numbers 784 to 1812 of SEQ ID NO: 2.

The "transcription activating domain of the transcription control factor operable in the host cell" described in (j) includes for example, transcription activating domain of GAL4 and E. coli-derived B42 acidic transcription activating domain. The "transcription coupling factor capable of ligand-dependently binding to the inventive receptor" is the transcription coupling factor capable of recognizing the complex of the inventive receptor and the ligand and binding to it and specifically, includes, for example, SRC1/NCoA1 (Onate, S. A. et al., Science, 1995, 270, 1354) and TIF2/GRIP1 (Voegel, J. J. et al., EMBO, J., 1996, 15, 3667). By linking in frame the DNA encoding the above-mentioned transcription activating domain and the DNA encoding the above-mentioned transcription coupling factor or the receptor binding domain of said transcription coupling factor, the DNA comprising "a nucleotide sequence encoding a fusion protein of the transcription activating domain of the transcription control factor operable in the host cell and the transcription coupling factor capable of ligand-dependently binding to the inventive receptor or the receptor binding domain of said transcription coupling factor" can be obtained. Note that, by replacing the components of the fusion protein described in (i) with that in (j), the "a fusion protein of the DNA binding domain of the transcription control factor operable in the host cell and the transcription coupling factor capable of ligand-dependently binding to the inventive receptor or the receptor binding domain of said transcription coupling factor" and the "a fusion protein of the transcription activating domain of the transcription control factor operable in the host cell and the inventive receptor or the ligand binding domain of said receptor" may be used. By linking the nucleotide sequence encoding each of the fusion proteins downstream of "a promoter operable in the host cell", a chimera gene described in (i) and a chimera gene described in (j) can be obtained. As such a promoter, for example, inducible promoters such as GAL1 promoter and constitutive expression promoters such as an ADH promoter, may be used if the host cell is a budding yeast cell.

For the reporter protein described in (k), any of luciferase, secretory alkaline phosphatase, β-galactositase, chloramphenicol acetyltransferase, and growth hormone can be used, among which, preferably, the reporter protein with relatively higher stability in the host cell is used. By linking a nucleotide sequence encoding said reporter protein downstream of a nucleotide sequence, to which the above-mentioned DNA binding domain is capable of binding; and a promoter capable of being activated by the bove-mentioned transcription activating domain, "the reporter gene in which a nucleotide sequence encoding a repoter protein is linked downstream of a nucleotide sequence to which the DNA binding domain described in (i) is capable of binding and a promoter capable of being activated by the transcription activating domain described in (j)" can be obtained. For example, the nucleotide sequence to which the GAL4 DNA binding domain can bind includes the GAL4 binding domain of the GALL promoter and the nucleotide sequence to which LexA can bind includes the LexA binding domain. The promoter activated by the GAL4 transcription activating domain includes, for example, an yeast-derived minimal TATA box sequence.

The above-mentioned chimera genes and a reporter gene are, for example, inserted each into the vectors and introduced into the same host cell to obtain the transformant. Note that the host cell, if having an intrinsic reporter gene which is available, may be used and in such a case, the step for introducing the reporter gene may be omitted. Alternatively, the transformant can be prepared using any of commercially available kits for preparing the two-hybrid system such as Matchmaker Two-hybrid System (Manufactured by Clontech Corp.) and CheckMate Mammalian Two-Hybrid System (Promega Corp.). As an example of the structure of the two-hybrid system where ligand-dependent formation of a complex comprising:

an estrogen receptor encoded by the inventive gene or the ligand binding domain of said receptor, and a transcription coupling factor capable of ligand-dependently binding to the receptor;

results in activation of transcription of a reporter gene, for example, the tansformant may be given, in said transformant the chimera genes described in the following (l) and (m) are introduced into the budding yeast Y190 strain (Manufactured by Clontech Corp.) containing a reporter gene in which a nucleotide sequence encoding LacZ is linked downstream of the intrinsic GAL1 UAS (upstream activating sequence) and the yeast-derived minimal TATA box sequence.

(l) A chimera gene in which a nucleotide sequence encoding a fusion protein of the DNA binding domain of GAL4 and the inventive receptor or the ligand binding domain of said receptor is linked downstream of the ADH1 promoter.

(m) A chimera gene in which a nucleotide sequence encoding a fusion protein of the transcription activating domain of GAL4 and the transcription coupling factor TIF1 capable of ligand-dependently binding to the inventive receptor or the receptor binding domain of the TIF1 is linked downstream of the ADH1 promote.

As mentioned above, while the prepared transformant being cultivated for, for example, several hours to several days, the test substance is added into the medium culture for making contact with the transformant to induce the formation of the complex of the estrogen receptor or the ligand binding domain of the estrogen receptor and the transcription coupling factor or the receptor binding domain of the transcription coupling factor, and the ability of transcription regulation of the complex is measured using the expression amount of the reporter gene as an indicator. For example, a luciferase reporter gene is used, and luciferin, the substrate of the luciferase, is added to a crude cell extract prepared from the transformant that has been in contact with the test substance, so that luminescence can be observed in an intensity proportional to the amount of the luciferase in the crude cell extract. Therefore, the intensity of the luminescence may be measured using a measuring apparatus such as a luminometer so that the amount of the luciferase and therefore the expression amount of the luciferase reporter gene can be determined. In a similar manner, under the condition that the transformant is not in contact with the test substance, a measurement is made on the expression amount of the reporter gene. The measured expression amount is compared with the amount measured under the test substance contact condition, so that the agonistic activity on the estrogen receptor, i.e., the ability to activate the estrogen receptor of a subsntance with an estrogen-like activity in the test substance can be evaluated. On the other hand, for example, under each of the condition that the transformant is in contact with the estrogen such as E2 and the condition that the transformant is in contact with the estrogen and the test substance at the same time, a measurement is made on the expression amount of the reporter gene in a similar manner to the above. The measurements under both conditions are compared with each other. If the expression amount under the condition that the transformant is in contact with the estrogen and the test substance is lower than that under the condition that the transformant is in contact with the estrogen, the test substance can be evaluated as having the antagonistic activity on the estrogen receptor, i.e., the anti-activation ability on the receptor.

The receptor binding assay using the inventive receptor enables the measurement of the ability of any chemical substance to bind to the inventive receptor, the quantification of the binding amount, and the analysis of the binding specificity or the binding strength. For example, a labeled ligand is preliminarily allowed to bind to the inventive receptor, which is recovered from the inventive transformant as described above. The test substance is then allowed to coexist with the labeled ligand so that the test substance competes with the labeled ligand. Depending on the affinity of each for the inventive estrogen receptor, the labeled ligand is released from the receptor. The amount of the labeled ligand bound to the receptor decreases, and therefore, the amount of the label bound to the receptor decreases. Thus, the label amount of the free form or the bound form of the labeled ligand may be monitored to indirectly determine the ability of the test substance to bind to the receptor.

For example, the labeled ligand may be tritium-labeled E2 or the like. The bound and free forms of the labeled ligand may be separated by hydroxyapatite method, glycerol density gradient ultracentrifugation or the like. The reaction system may broadly be classified into three groups. The first group includes a system in which only a solvent is added to the labeled ligand-bound estrogen receptor and corresponds to the system in which the addition amount of the test substance is zero. In this system, the label amount of the bound form of the labeled ligand represents the total amount of the labeled ligand bound to the estrogen receptor (the total binding amount). The second group includes a system in which for example, an unlabeled ligand is added to the labeled ligand-bound estrogen receptor in such a concentration that the estrogen receptor is saturated with the unlabeled ligand so as to have no capacity for binding to the labeled ligand (for example, 10 μM). In this system, the label amount of the bound form of the labeled ligand is determined as the amount of the labeled ligand nonspecifically bound to the estrogen receptor (the nonspecific binding amount). Therefore, the amount of the labeled ligand specifically bound to the inventive estrogen receptor (the specific binding amount) is calculated by subtracting the nonspecific binding amount from the total binding amount. The third group includes a system in which the test substance is added to the labeled ligand-bound estrogen receptor at a final concentration of 10 μM, for example (such a concentration may arbitrarily be altered depending on the purpose). If the test substance has the ability to bind to the estrogen receptor, the label amount of the bound form of the labeled ligand obtained in this system will be smaller than the specific binding amount obtained as described above under the condition that the addition amount of the test material is zero. Thus, such a receptor binding assay may be performed to determine the ability of the test substance to bind to the inventive receptor. If the test substance include different substances, the assay can also determine whether the test substance includes any substance that has an affinity for the estrogen receptor. If the ability of the test substance to bind to the inventive receptor should be evaluated in a more detailed manner, for example, the test substance may be added at different concentrations in the third group in the process of the receptor binding assay descrived above. For example, the label amount of the bound form of the labeled ligand may be determined to produce the amounts of the bound and free forms of the ligand, respectively, and then the results may be subjected to the Scatchard analysis so that the binding affinity, the binding specificity, the binding capacity, or the like can be evaluated between the test substance and the inventive receptor.

The reporter assay, the two-hybrid system, and the receptor binding assay of the present invention can be applied to safety evaluation of chemical substances, detection of environmental estrogen-like substances, and the like.

EXAMPLES

The present invention is more specifically described with reference to the examples below, but such examples are not intended to limit the scope of the present invention.

Example 1

Obtaining the Inventive Gene

From liver tissue of fathead minnow, total RNA was prepared in accordance with the phenol-chloroform-isoamyl alcohol technique (Plant Cell Physiol. 36(1): pp 85-93 (1995)). The yield of the total RNA was approximately 2.3 mg. From approximately 500 μg of the total RNA, poly(A) $^+$RNA was prepared using Oligotex(dT)$_{30}$-Super (manufactured by Takara Shuzo Co., Ltd.). The yield of poly(A) $^+$RNA was approximately 12 μg. Then, a cDNA library was prepared in accordance with the Gubler and Hoffman method. In this step, first, single-stranded cDNAs were synthesized using 2.0 μg of poly(A) $^+$RNA, Oligo(dT)$_{18}$-linker primer ((GA)$_{10}$ACGCGTCGACTCGAGCGGCCGCGGACCG (T)$_{18}$, contaning an XhoI recognition sequence) (manufactured by Takara Shuzo Co., Ltd.), RAV-2 RTase (manufactured by Takara Shuzo Co., Ltd.) and SuperScriptII RTase (manufactured by Gibco-BRL) and by adding 5-methyl dCTP. Double-stranded cDNAs were synthesized from the resultant single-stranded cDNAs and the both ends of the synthesized double-stranded cDNAs were made blunt, at which an EcoRI-NotI-BamHI adaptor (code 4510, manufactured by Takara Shuzo Co., Ltd.) was ligated. The resultant DNAs were digested with a restriction enzyme XhoI and dispensed in a spin column to separate low molecular weight DNA components, and ligated with λZAPII digested with EcoRI and XhoI. Using the resultant DNA and the in vitro packaging kit (manufactured by Stratagene Inc.), in vitro packaging was performed to obtain a cDNA library. Using $E.$ $coli$ XL1 Blue MRF' strain (manufactured by Stratagene Inc.) as a host cell, said cDNA library was titrated, estimating that the content of the insert was approximately 75% based on the appearance rates of blue and white colonies, respectively.

An oligonucleotide comprising the nucleotide sequence of SEQ ID NO: 6 and an oligonucleotide comprising the nucleotide sequence of SEQ ID NO: 7 were synthesized. PCR (30 cycles conducted wherein one cycle involves incubation at 94° C. for one minute, 55° C. for one more minute, and then at 74° C. for 2.5 minutes) was performed using said oligonucleotides as primers and the double-stranded cDNA library prepared from liver of fathead minnow as described above as a template. Approximately 400 bp of amplified DNA was subcloned into a TA cloning vector prepared using a EcoRV site of pBluescriptII SK(+) vector (manufactured by Stratagene Inc.) and the nucleotide sequence of the DNA that was inserted into the vector contained in the resultant clone was analyzed. The DNA comprising the nucleotide sequence of SEQ ID NO: 3 was selected and said DNA was purified from the clone containing it. By directly labeling the purified DNA with a thermostable alkaline phosphatase using the AlkPhos Direct system (manufactured by Amersham Pharmacia Biotech Inc. Inc.), the probe was prepared.

The library prepared as described above was introduced into $E.$ $coli$ XL1 Blue MRF' strain and an aliquot of approximately 50,000 clones was plated on each of LB plates (1% Bacto-Triptone, 0.5% Yeast extract, 0.5% NaCl, 1.5% agar) with 150 mm in diameter to form plaques. A total of six these plates were prepared for making screening on 300,000 clones as described below. From the individual plates, phage DNA was moved onto the Hybond N+ membranes (manufactured by Amersham Pharmacia Biotech), and said membranes were immersed in a denaturing solution (1.5 M NaCl, 0.5 N NaOH) for five minutes and then in a neutralizing solution (1.5 M NaCl, 0.5 M Tris-HCl (pH 7.2), 1 mM EDTA) for ten minutes, and dried. These membranes were further incubated at 80° C. for two hours, whereby immobilizing the DNA on the membranes. Using the resultant membranes and the above-mentioned probe, screening was made by hybridization in accordance with the AlkPhos Direct system protocol. Namely, the above-mentioned membranes were immersed in the hybridization solution containing 0.5 M NaCl (manufactured by Amersham Pharmacia Biotech, 5 ng probe/ml) and incubated at 55° C. for 16 hours. Then, the membranes were incubated in a primary washing buffer (50 mM sodium phosphate buffer (pH 7.0) containing 2 M urea, 0.1% SDS, 150 mM NaCl, 1 mM $MgCl_2$, and 0.2% blocking reagent) at 60° C. for ten minutes and then incubated in the fresh primary washing buffer at 65° C. for ten more minutes. Moreover, the resultant membranes were incubated in a secondary washing buffer (50 mM sodium phosphate buffer containing 100 mM NaCl and 2 mM $MgCl_2$) at room temperature for five minutes and then incubated in a fresh secondary washing buffer at room temperature for five more minutes. On the resultant membranes, an attempt of detecting any chemiluminescent signals arisen from enzymatic action of alkaline phosphatase on a substrate was made using CDP-Star contained in the AlkPhos Direct system as a substrate and treating in accordance with the manual description attached to the system. For films, Hyperfilm ECL (manufactured by Amarsham Pharmacia Biotech) was used. Ten positive clones were individually selected starting from one with the strongest signal. The selected positive clones were collected using sterilized chips, suspended in a SM buffer (50 mM Tris-HCl (pH 7.5),100 mM NaCl, $MgSO_4.H_2O$, 0.01% gelatine), and kept at 4° C. The resultant positive clones were cultivated, and an aliquot of approximate 1,000 to 1,500 clones was plated on each of LB plates with approximate 90 mm in diameter (a total of ten plates) for forming plaques, and in the same manner as that mentioned above, screening was made by hybridization. As a result, among the ten positive clones, a positive signal was detected on three clones, which were collected as positive clones. Then, these three clones were cultivated, an aliquot of approximate 200 clones was plated on each of LB plate with approximate 90 mm in diameter for forming plaques, and in the same manner as that mentioned above, screening was made by hybridization. In this screening process, three clones with the positive signal detected were isolated. From the vector contained in said positive clone, a plasmid where the DNA inserted into said vector was cloned into pBluescript SK(−) was obtained using the in vivo excision system in accordance with the protocol supplied with the λZAPII vector kit (manufactured by Stratagene Inc.). On three cloned DNAs, nucleotide sequence analysis was made with the Primer Walking technique. The result of the analysis showed that one of said DNAs contained the nucleotide sequence represented by nucleotide numbers 458 to 1965 in the nucleotide sequence of SEQ ID NO: 2 (hereinafter, the plasmid where said DNA is cloned into pBluescript SK(−) is referred to as A2209), and that another one of said DNAs contained the nucleotide sequence represented by nucleotide numbers 1 to 1133 in the nucleotide sequence of SEQ ID NO: 2 (hereinafter, the plasmid where said DNA is cloned into pBluescript SK(−) is referred to as A0902). These nucleotide sequences were linked to each other with the same parts overlapped, so that the nucleotide sequence of SEQ ID NO: 2 was obtained, and such a nucleotide sequence was found to encode the amino acid sequence of SEQ ID NO: 1. $E.$ $coli$ DH5α strain containing the plasmid A2209 was deposited as an International deposition under the Budapest Treaty under its deposit number FERM BP-7103 in International Patent Organism Depositary (IPOD) (National Institute of Advanced Industrial Science and Technology, Chuo $6^{th}$, Higashi 1-1, Tsukuba, Ibaraki (Japan), postal code 305-8566) on Mar. 23, 2000.

Example 2

Construction of the Inventive Vector for Expression in Animal Cell

Two μg of DNA of expression plasmid pRc/RSV (manufactured by Invitrogen) containing RSV promoter was digested all night at 37° C. with restriction enzymes Spe I (10 U) and Xba I (10 U), and then on the resultant digested DNA 5 U of alkaline phosphatase (BAP) was reacted at 65° C. for one hour. Gel electrophoresis was performed on this plasmid using the agarose (Agarose S manufactured by Nippon Gene Co., Ltd.) and the DNA was collected from the band with a length of 5 to 6 kbp using Gene Clean (manufactured by Funakoshi Co., Ltd.) for preparing the vector DNA. On the other hand, from liver of fathead minnow, total RNA was prepared using Trizol reagent (manufactured by GIBCO-BRL) in accordance with the supplied manual. Using the prepared total RNA and a random primer supplied with the RT-PCR kit (AMV) ver. 2.1 (manufactured by Takara Shuzo Co., Ltd.) cDNAs were prepared in accordance with the manual description attached to the kit. PCR (25 cycles conducted wherein one cycle involves incubation at 94° C. for one minute, 53° C. for two more minute, and then at 74° C. for 2.0 minutes) was performed with LA-Taq (manufactured by Takara Shuzo Co., Ltd) using the prepared cDNAs as a template and using an oligonucleotide comprising the nucleotide sequence of SEQ ID NO: 8 and an oligonucleotide comprising the nucleotide sequence of SEQ ID NO: 9 for amplifying the DNA of the inventive gene. The amplified DNA was treated with chloroform/phenol and recovered by ethanol precipitation. The recovered DNA was digested at 37° C. for five hours with restriction enzymes Spe I and XbaI. The resultant digest was separated by electrophoresis using 1% of agarose gel for extracting the gel component containing approximately 2.0 kbp of DNA and the DNA contained in the gel component was purified with GENECLEAN (manufactured by Funakoshi Co., Ltd.). Approximately 100 ng of the purified DNA was mixed with approximately 50 ng of vector DNA prepared as described above, and was ligated using Ligation kit ver. 2 (manufactured by Takara Shuzo Co., Ltd) at 16° C. for approximately three hours. The DNA contained in the reaction solution was transduced into the *E. coli* DH5α strain competent cell (manufactured by TOYOBO CO., LTD.) in accordance with the supplied instructions. The plasmid DNA was prepared from the colony indicating ampicillin-resistance by the alkaline method and then the nucleotide sequence of the resultant plasmid DNA was analyzed. The plasmid with the structure in which the inventive gene was inserted between the Spe I restriction site and the Xba I restriction site of pRc/RSV was selected and termed pRc/RSVFMERα.

Example 3

Reporter Assay Using the Inventive Gene (1) Preparation of a Reporter Plasmid for Reporter Assay

*Xenopus* genome DNA was purified with Isogen reagent (Nippon Gene) in accordance with the supplied manual. With the purified genome DNA as a template, PCR was performed according to the report by Walker et al. (Nucleic acid Res. (1984) 12, 8611-8626) to amplify DNA which includes the sequence upstream of the *Xenopus vitellogenin* gene from the TATA box to the estrogen receptor response element sequence. The amplified DNA was recovered and then treated with Blunting kit (Takara) to have blunt ends (hereinafter the resulting DNA is referred to as ERE DNA).

Two oligonucleotides each having a nucleotide sequence derived from a nucleotide sequence near the TATA box and a leader sequence of mouse metallothionein I gene (Genbank Accession No.J00605): i.e., an oligonucleotide comprising the nucleotide sequence of SEQ ID NO:10 and an oligonucleotide comprising the nucleotide sequence of SEQ ID NO:11, were allowed to anneal each other to form a double stranded DNA, both ends of which was then phosphorylated with T4 polynucleotide kinase (hereinafter the resulting DNA is referred to as TATA DNA). Firefly luciferase gene-containing plasmid pGL3 (Promega) was digested with restriction enzymes Bgl II and Hind III and then mixed with Bacterial alkaline phosphatase (BAP) and incubated at 65° C. for 1 hour. The incubated solution was then subjected to electrophoresis using a low melting point agarose (AgaroseL, Nippon Gene), and a Bgl II-Hind III fragment DNA containing the pGL3-derived luciferase gene was recovered. About 100 ng of the recovered DNA and 1 μg of the TATA DNA were mixed and ligated with T4 ligase to form plasmid pGL3-TATA. The pGL3-TATA was digested with restriction enzyme Sma I and then mixed with BAP and incubated at 65° C. for 1 hour. The incubated solution was then subjected to low melting point agarose gel electrophoresis, and a DNA was recovered from gel component containing DNA band. About 100 ng of the recovered DNA and about 1 μg of the ERE DNA were mixed and allowed to react with T4 ligase. From the reaction solution, the DNA was then introduced into *E. coli* DH5α strain competent cells (TOYOBO). From each of several ampicillin-resistant *E. coli* colonies, a plasmid DNA was prepared. Each prepared DNA was digested with restriction enzymes Kpn I and Xho I, and the resulting digest was analyzed by agarose gel electrophoresis. A plasmid with a structure in which one copy of the ERE DNA was introduced in the Sma I site of pGL3-TATA was termed plasmid pGL3-TATA-ERE, and another plasmid with a structure in which five copies of the ERE DNA were introduced in the Sma I site was termed plasmid pGL3-TATA-ERE×5.

(2) Reporter Assay Using a Transient Expression Line

Figure 2:
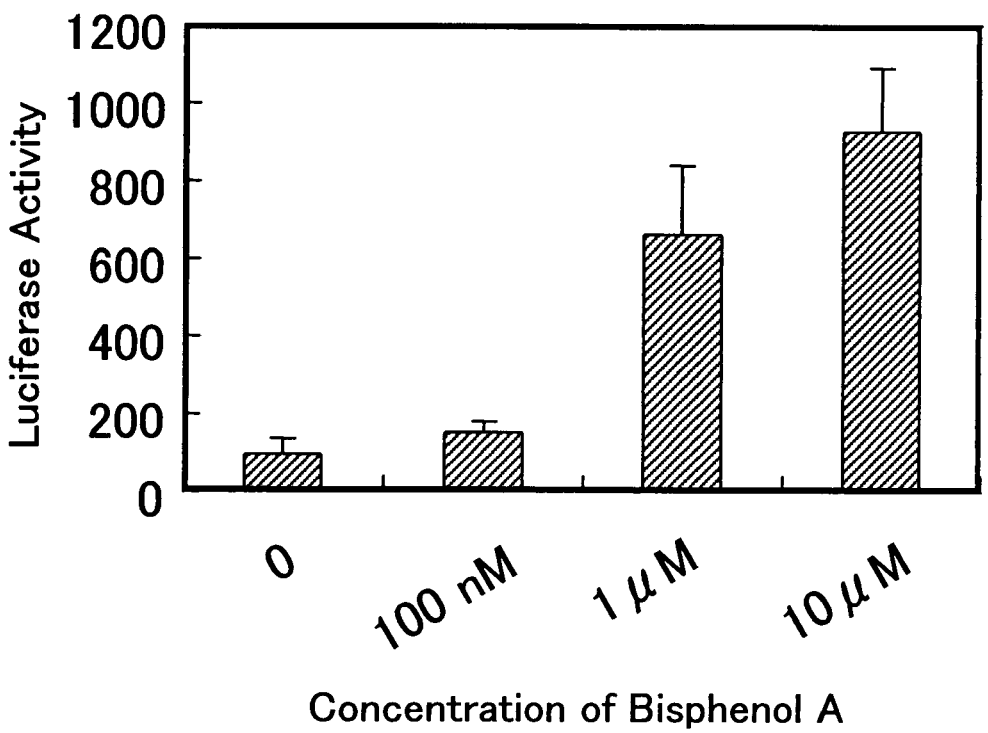
FIG. 2 is a diagram showing a result of measuring the ability of bisphenol A to activate the estrogen receptor activity by the reporter assay using the inventive gene. The abscissa axis represents the concentration of bisphenol A in each experimental section. The left end column indicated by O corresponds to an experimental section in which DMSO was added at a final concentration of 0.1% in place of the DMSO solution of bisphenol A (bisphenol A-free section). The ordinate axis represents the luciferase activity value, where the luciferase activity value of the bisphenol A-free section is normalized as 100.
Figure 3:
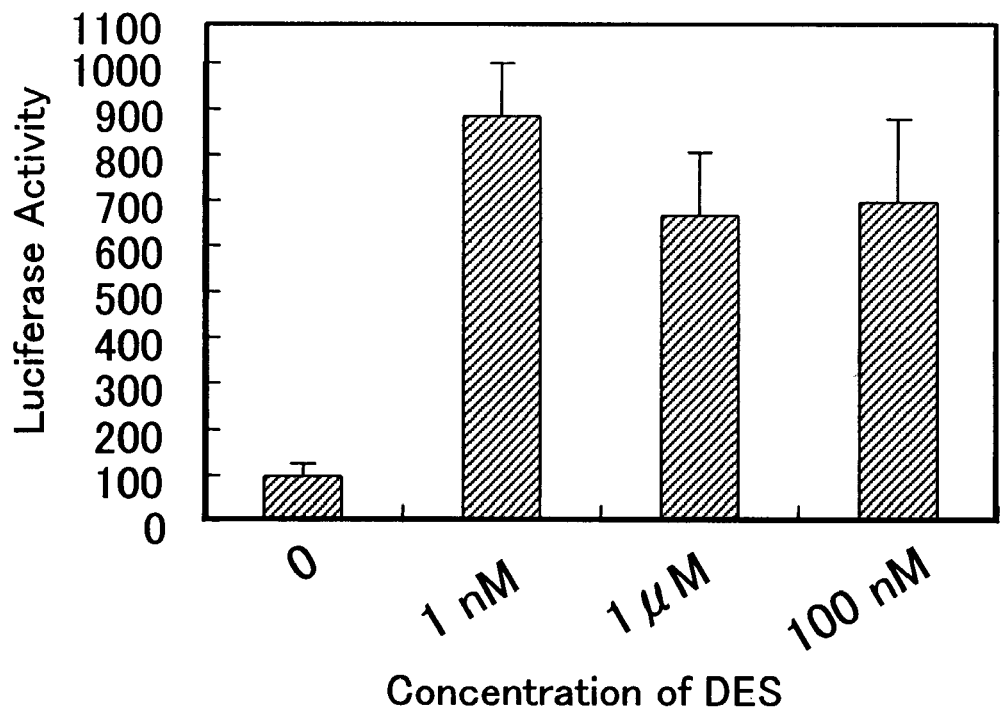
FIG. 3 is a diagram showing a result of measuring the ability of diethylstilbestrol (DES) to activate the estrogen receptor activity by the reporter assay using the inventive gene. The abscissa axis represents the concentration of DES in each experimental section. The left end column indicated by O corresponds to an experimental section in which DMSO was added at a final concentration of 0.1% in place of the DMSO solution of DES (DES-free section). The ordinate axis represents the luciferase activity value, where the luciferase activity value of the DES-free section is normalized as 100.
Figure 4:
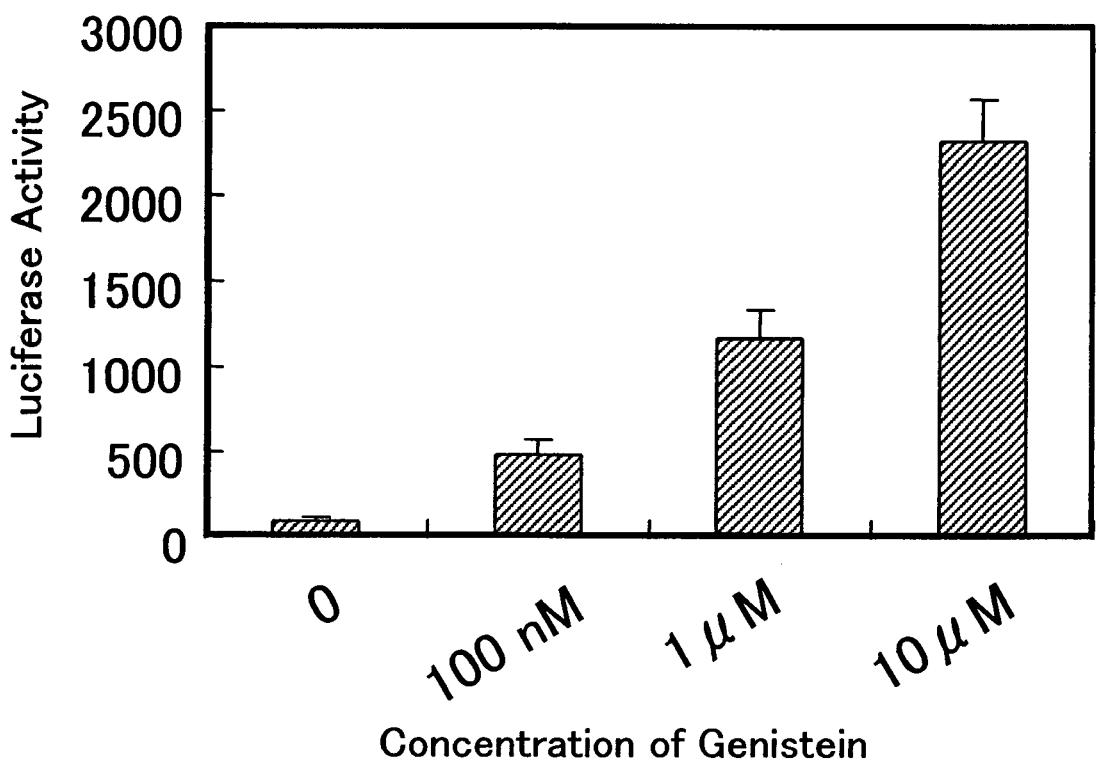
FIG. 4 is a diagram showing a result of measuring the ability of genistein to activate the estrogen receptor activity by the reporter assay using the inventive gene. The abscissa axis represents the concentration of genistein in each experimental section. The left end column indicated by O corresponds to an experimental section in which DMSO was added at a final concentration of 0.1% in place of the DMSO solution of genistein (genistein-free section). The ordinate axis represents the luciferase activity value, where the luciferase activity value of the genistein-free section is normalized as 100.
Figure 5:
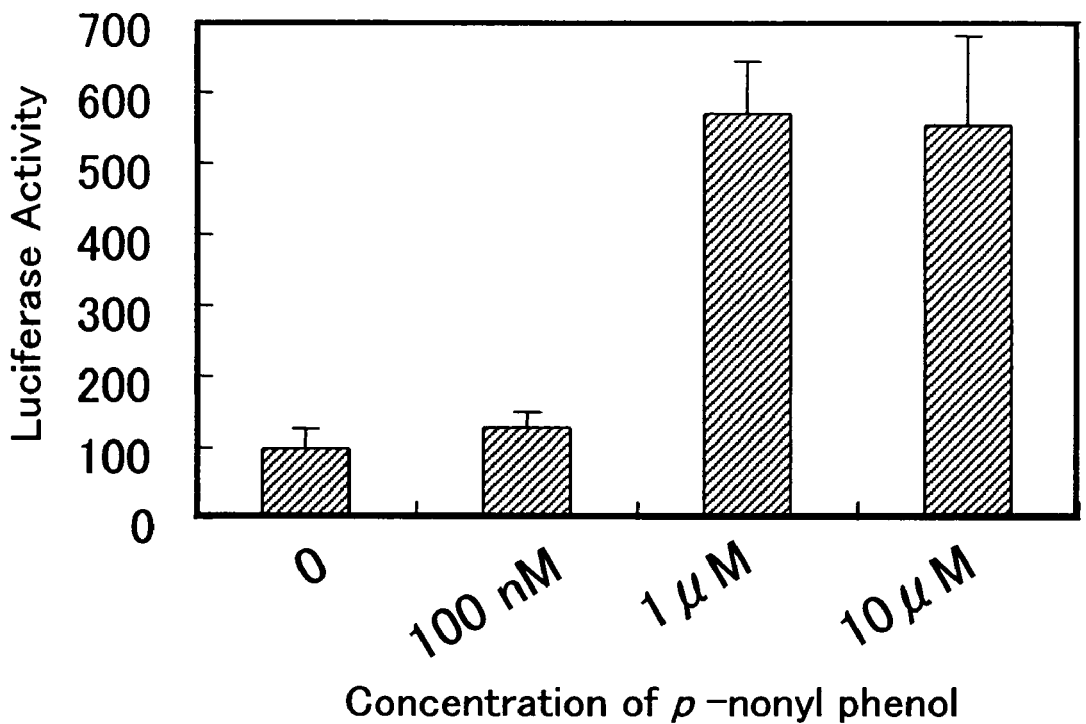
FIG. 5 is a diagram showing a result of measuring the ability of p-nonyl phenol to activate the estrogen receptor activity by the reporter assay using the inventive gene. The abscissa axis represents the concentration of p-nonyl phenol in each experimental section. The left end column indicated by O corresponds to an experimental section in which DMSO was added at a final concentration of 0.1% in place of the DMSO solution of p-nonyl phenol (p-nonyl phenol-free section). The ordinate axis represents the luciferase activity value, where the luciferase activity value of the p-nonyl phenol-free section is normalized as 100.

Approximately $2\times10^6$ HeLa cells were inoculated on 10 cm plates and incubated in an E-MEM medium containing 10% of charcoal dextran-treated FBS (hereafter, referred to as FBS) under 5% of $CO_2$ at 37° C. for one day. Then, 3.75 μg of pRc/RSVFMERα and 3.75 μg of pGL3-TATA-ERE×5 were transduced together into the cells using Lipofectamine (manufactured by Life Technologies Co., Ltd.) in accordance with the protocol supplied with it. It was incubated at 37° C. for 16 hours, the medium was replaced with a fresh one, and the incubation was continued for further three hours. Then, the cells were collected, suspended in the E-MEM medium containing 10% of FBS to disperse, and inoculated on 96-well plates with various concentrations of estradiol (manufactured by Wako Pure Chemical Industries, Ltd., final concentration of 10 pM to 1 μM), bisphenol A (manufactured by Wako Pure Chemical Industries, Ltd., final concentration of 100 nM to 10 μM), diethylstilbestrol (DES) (manufactured by Nacalai Tesque, Inc., final concentration of 1 nM to 100 nM), genistein (manufactured by Wako Pure Chemical Industries, Ltd., final concentration of 100 nM to 10 μM) or p-nonyl phenol (manufactured by Kanto Kagaku, final concentration of 100 nM to 10 μM), all of which were already dissolved with DMSO (final DMSO concentration of 0.1%). The 96-well plates with the cells inoculated on was incubated at 37° C. for approximately 40 hours and an aliquot (50 μl/well) of a cell resolvent PGC50 (manufactured by Nippon Gene Co., Ltd.) diluted to ⅕ concentration was added onto them, and left at room temperature for 30 minutes while carefully shaking them at times to lyse the cells. An aliquot (10 μl) of cell lysate prepared as described above was collected on the white 96-well sample plates (manufactured by BERTHOLD) and luminescence levels were immediately measured for five seconds using a luminometer LB96p with a auto matrix injector (manufactured by BERTHOD) while an aliquot (50 μl/well) of enzyme substrate solution PGL100 (manufactured by Nippon Gene Co., Ltd.) was being added. The result is shown in FIGS. 1 to 5. The activation ability of test substances on estrogen receptor could be measured by the luciferase reporter assay using the inventive gene.

(3) Preparation of the Transformant with the Inventive Gene Transduced into its Chromosome for Reporter Assay The plasmid pUCSV-BSD (purchased from Funakoshi) is digested with BamHI to prepare a DNA coding for a blasticidin S deaminase gene expression cassette. Further, the plasmid pGL3-TATA-ERE obtained in Example 3(1) is digested with BamHI and treated with BAP. The prepared DNA coding for a blasticidin S deaminase gene expression cassette is then mixed with the restriction digested pGL3-TATA-ERE. The resulting DNA mixture is allowed to react with T4 ligase. The DNA is then introduced from the reaction solution into E. coli DH5α competent cells (TOYOBO). An ampicillin-resistant colonies are isolated, and a plasmid DNA is prepared from the each colony. The prepared DNA are digested with restriction enzyme BamHI, and the resulting digests are analyzed by agarose gel electrophoresis. A plasmid with a structure in which the blasticidin S deaminase gene expression cassette is inserted in the BamHI restriction site of plasmid pGL3-TATA-ERE is selected and named plasmid pGL3-TATA-ERE-BSD.

The DNA of produced plasmid pGL3-TATA-ERE-BSD and DNA of plasmid pRc/RSVFMERα obtained in Example 2 are each linearized and then introduced into HeLa cells to obtain a transformant in which these DNAs are introduced into the host cell chromosome.

DNA of plasmid pGL3-TATA-ERE-BSD and DNA of plasmid pRc/RSVFMERα are each digested with Sal I. HeLa cells are cultured on plates about 10 cm in diameter (Falcon) with a 10% FBS-containing DMEM medium (Nissui Pharmaceutical) at 37° C. under 5% $CO_2$. About $5 \times 10^5$ cells are cultured for 1 day. The resulting cells are transfected simultaneously with the above linearized DNAs by lipofection method using lipofectin (GIBCO). The lipofection method is performed according to the manual description attached to the lipofectin under the following conditions: a treating time of 5 hours, the total amount of the linearized DNAs of 7 μg (each 3.5 μg) per plate, and a lipofectin amount of 20 μl/plate. After the lipofection, the cells are cultured in situ in the 10% FBS-containing DMEM medium for 3 days. The cells are peeled off from the plate by trypsin treatment and then divided into 10 aliquots, inoculated on 10 plates, respectively, and cultured overnight. G418 (Sigma) is then added to the culture at a final concentration of 400 μg/ml. Blasticidin S is also added to the culture at a final concentration of 8 μg/ml, and the cultivation is further carried out. After one week, the medium is replaced with a fresh one containing G418 and blasticidin S each at the same concentration, and the cultivation is further carried out. After a week, the same process is carried out again. After another week, the plates are observed with an inverted microscope, and 30 colonies with a diameter of several mm are each transferred to each well of a 96-well view plate (Berthold) to which a medium has been added to each well in advance, and the cultivation is further carried out. Before grown in a confluent state, the cells are peeled off by trypsin treatment, collected, divided into 3 aliquots, and inoculated on new three 96-well view plates, respectively. The cells on one plate are subcultured. E2 is added to one of the remaining two plates at a final concentration of 50 nM, and nothing is added to the other plate. The cells on each plate are cultured for 2 days. After the 2 days, each culture supernatant is removed from each plate, and the cells are washed with 200 μl/well of PBS(−) twice. In order to lyse the cells, cytolytic agent PGC50 (Nippon Gene) 5-fold diluted was then added to each view plate in an amount of 20 μl/well and allowed to stand at room temperature for 30 minutes. The plates are each placed in Luminometer LB96p equipped with an automatic enzyme substrate injector (Berthold). While 50 μl of enzyme substrate solution PGL1000 (Nippon Gene) is automatically added to each well, the luciferase activity is measured. When the luciferase activity of the E2-containing experimental section is at least twice as high as that of the E2-free experimental section, the transformant cells are selected and collected.

(4) Reporter Assay Using the Transformant with the Inventive Gene Transduced into its Chromosome The transformant prepared in Example 3(3) is inoculated on a 24-well plate at a density of about $4 \times 10^4$ cells/well and cultured under 5% $CO_2$ at 37° C. for 1 day in an E-MEM medium containing 10% of charcoal dextran-treated FBS, 400 μg/ml of G418, and 8 μg/ml of blasticidin S (hereinafter referred to as the FBS and antibiotic-containing E-MEM medium). A test substance DMSO (Wako Pure Chemical) solution is added to the FBS and antibiotic-containing E-MEM medium in different amounts so as to provide final test substance concentrations of 1 nM to 50 μM. Alternatively, DMSO is added to the FBS and antibiotic-containing E-MEM medium in the same amount as that of above each test substance solution. Alternatively, a DMSO solution of E2 is added to the FBS and antibiotic-containing E-MEM medium so as to provide an E2 final concentration of 1 μM. The above cell culture supernatant is replaced with each of the above resulting mediums. The cell culture is held in a $CO_2$ incubator for 24 hours, and then the culture supernatant is removed from the plate. While attention is paid not to peel off the adhering cells from the plate, the cells are washed with 1 ml/well of PBS(−) twice. For the purpose of lysing the cells, cytolytic agent PGC50 (Nippon Gene) 5-fold diluted is added to the plate in an amount of 50 μl/well and allowed to stand at room temperature for 30 minutes while sometimes gently shaken. The resulting lysis solution is placed on a 96-well white sample plate (Berthold) in an amount of 10 μl/well. In Luminometer LB96p equipped with an automatic substrate injector (Berthold), enzyme substrate solution PGL100 (Nippon Gene) is added to the plate in an amount of 50 μl/well, and immediately, the luminescence intensity from each well is measured for 5 seconds.

By the luciferase reporter assay using the transformant with the inventive gene transduced into its chromosome as descried above, the test substances containing the substances having the estrogen receptor activating ability can be detected.

Example 4

Two-Hybrid System Using the Inventive Gene (1) Preparation of the Vector Containing the Chimera Gene Coding the Fusion Protein of the Ligand Binding Domain of the Inventive Receptor and the DNA Binding Domain of the Ttranscription Control Factor PCR (25 cycles conducted wherein one cycle involves incubation at 94° C. for one minute, 55° C. for one more minute, and then at 74° C. for 1.5 minutes) was performed using the plasmid A2209 as a template, and using an oligonucleotide comprising the nucleotide sequence of SEQ ID NO: 12 and an oligonucleotide comprising the nucleotide sequence of SEQ ID NO: 13 as primers for amplifying the DNA comprising the nucleotide sequence represented by nucleotide numbers 784 to 1812 in the nucleotide sequence of SEQ ID NO: 2, thereby coding the ligand binding domain of the inventive receptor.

The amplified DNA was treated with chloroform/phenol and then precipitated with ethanol. The precipitate was centrifugally washed with 70% ethanol and then dried. The DNA was dissolved with TE added and then digested with restriction enzymes EcoRI and SalI at 37° C. for about 5 hours. The digest was subjected to 1% agarose gel electrophoresis and separated. About 1 kbp DNA-containing part of the gel was cut out, and the DNA was recovered from the part using GENECLEAN (manufactured by Funakoshi Co., Ltd.). Vector pGBT9 (manufactured by Clontech) (about 50 ng), for the production of the fusion protein with the DNA binding domain of GAL4 protein, was digested with EcoRI and SalI and then subjected to agarose gel electrophoresis. The EcoRI and SalI-digested vector DNA was then recovered using GENECLEAN (manufactured by Funakoshi Co., Ltd.). The recovered vector DNA and about 10 ng of the above recovered DNA were mixed with each other. A ligation solution (Ligation Kit, manufactured by Takara Shuzo Co., Ltd.) was added to the mixture in the same volume and incubated at 16° C. for about 5 hours. The resulting mixture was then introduced into competent DH5α cells (manufactured by TOYOBO CO., LTD.) in accordance with the supplied instructions. An ampicillin-resistant colony was isolated, and a plasmid DNA was prepared from the colony by alkaline method. The nucleotide sequence of the prepared plasmid DNA was confirmed and then named pGBT9-FMERαLID. This plasmid can be applied to the two-hybrid assay using the budding yeast as the host cell.

(2) Preparing the Vector Containing the Chimera Gene Coding the Fusion Protein of the Receptor Binding Domain of the Transcription Coupling Factor and Transcription Activating Domain of the Transcription Coupling Factor A cDNA was produced using a human brain-derived mRNA (Clontech) and RT-PCR kit (Takara) in accordance with the protocol attached to the products. PCR was performed using the produced cDNA as a template, and using an oligonucleotide comprising the nucleotide sequence of SEQ ID NO:14 and an oligonucleotide comprising the nucleotide sequence of SEQ ID NO:15 as primers (the PCR reaction conditions: 30 cycles of 94° C. for 1 minute, 55° C. for 1 minute, and 72° C. for 2.5 minutes). The PCR amplified a DNA coding for the amino acid sequence between amino acids 624 and 1287 from the amino terminal end of transcription coupling factor TIF2. The amplified DNA was treated with chloroform/phenol and then precipitated with ethanol. The precipitate was centrifugally washed with 70% ethanol and then dried. The DNA was dissolved with TE added and then digested with restriction enzymes EcoRI and BglII at 37° C. for 5 hours. The digest was subjected to 1% agarose gel electrophoresis and separated. About 2.0 kbp DNA-containing part of the gel was cut out, and the DNA was recovered from the part using GENECLEAN (Funakoshi). Vector pGAD424 (Clontech) (about 50 ng), for the production of the fusion protein with the transcription activating domain of GAL4 protein, was digested with EcoRI and BamHI and then subjected to agarose gel electrophoresis. The EcoRI and BamHI-digested vector DNA was then recovered using GENECLEAN (Funakoshi). The recovered vector DNA and about 10 ng of the above-recovered DNA were mixed with each other. A ligation solution (Ligation Kit, Takara) was added to the mixture in the same volume and incubated at 16° C. for about 1 hour. The resulting mixture was then introduced into E. coli DH5α competent cells (TOYOBO) in accordance with the supplied instructions. An ampicillin-resistant colony was isolated, and a plasmid DNA was prepared from the colony by alkaline method. The nucleotide sequence of the prepared plasmid DNA was confirmed and then named pGAD424-TIF2RID. This plasmid can be applied to the two-hybrid assay using the budding yeast as the host cell.

(3) Preparing the Two-hybrid System Using Budding Yeast Cells as Host Cells

Yeast Y190 (Clontech) was shake-cultured in YPD medium at 30° C. overnight according to the manual of Matchmaker Two-Hybrid System (Clontech). The cultured yeast cells were collected and then transfected with pGBT9-FMERαLID obtained in Example 4(1) and pGAD424-TIF2RID obtained in Example 4(2) using Yeastmaker yeast transformation system (Clontech). The two plasmid-introduced yeast cells were inoculated on a tryptophan and leucine-free SD nutrient agar and cultured at 30° C. for about 2 days. After the culture was completed, grown colonies were selected, applied again on the tryptophan and leucine-free SD nutrient agar, and cultured at 30° C. for about 2 days.

Figure 6:
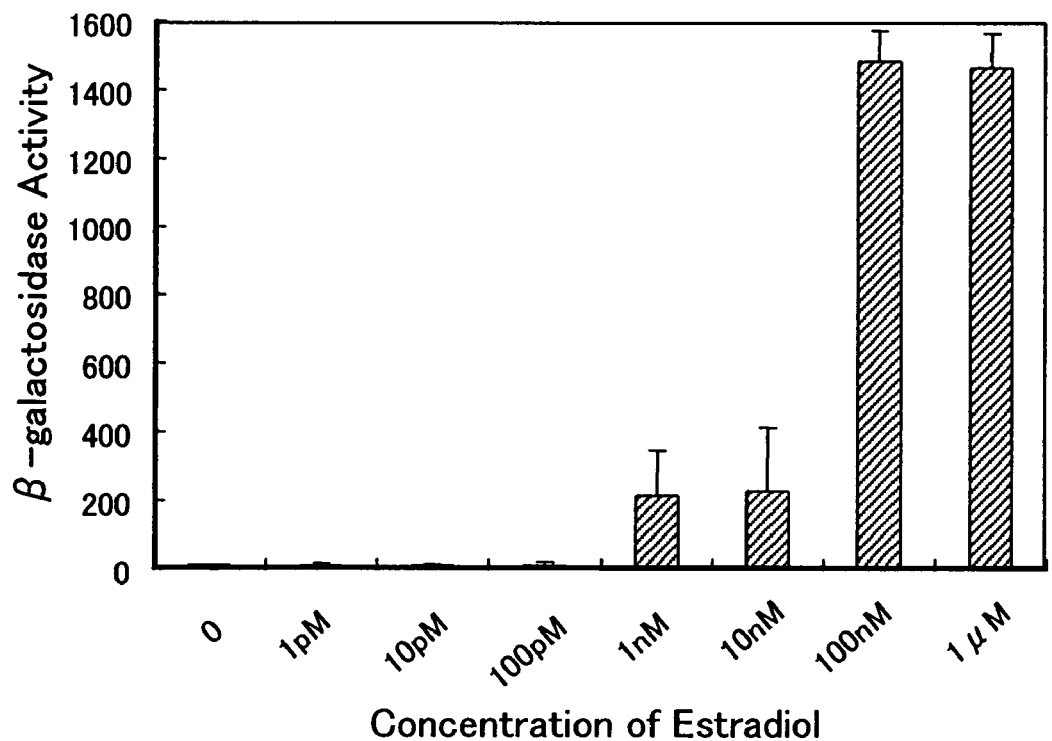
FIG. 6 is a diagram showing a result of measuring the ability of E2 to activate the estrogen receptor activity by the two-hybrid system using DNA enconding the ligand binding domain of the inventive receptor. The abscissa axis represents the concentration of E2 in each experimental section. The left end column indicated by O corresponds to an experimental section in which DMSO was added at a final concentration of 0.1% in place of the DMSO solution of E2 (E2-free section). The ordinate axis represents the β-galactosidase activity value, where the β-galactosidase activity value of the E2-free section is normalized as 1.
Figure 7:
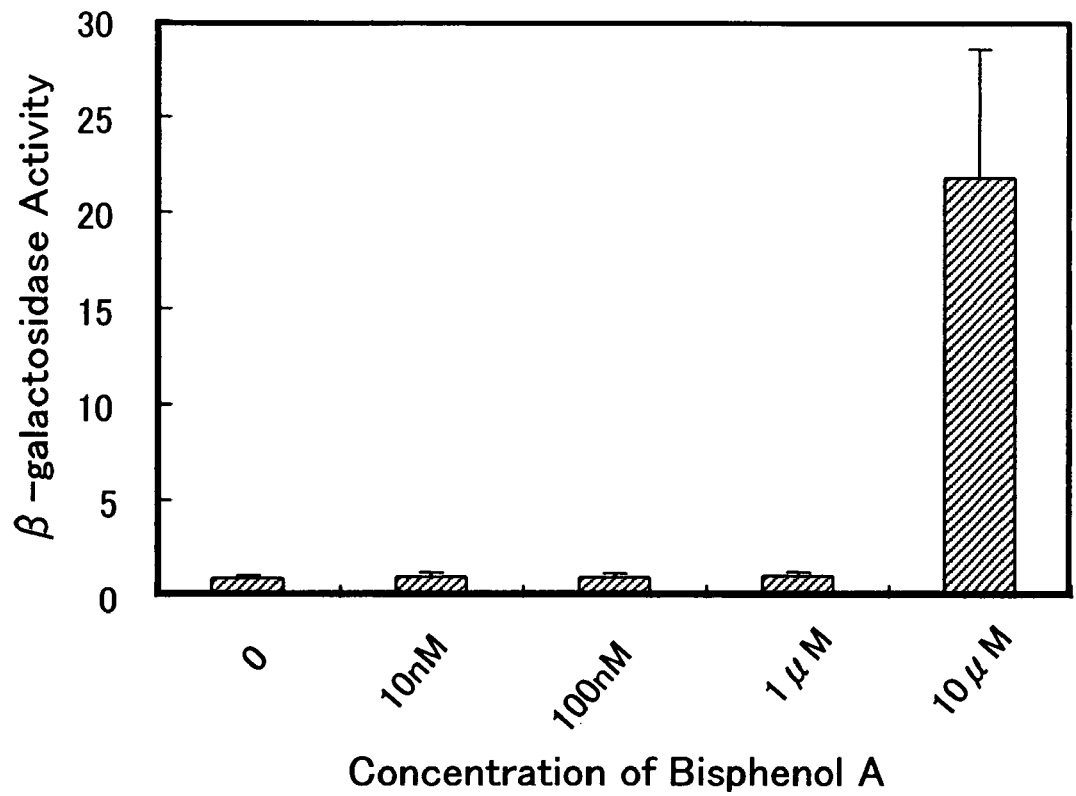
FIG. 7 is a diagram showing a result of measuring the ability of bisphenol A to activate the estrogen receptor activity by the two-hybrid system using DNA encoding the ligand binding domain of the inventive receptor. The abscissa axis represents the concentration of bisphenol A in each experimental section. The left end column indicated by O corresponds to an experimental section in which DMSO was added at a final concentration of 0.1% in place of the DMSO solution of bisphenol A (bisphenol A-free section). The ordinate axis represents the β-galactosidase activity value, where the β-galactosidase activity value of the bisphenol A-free section is normalized as 1.
Figure 8:
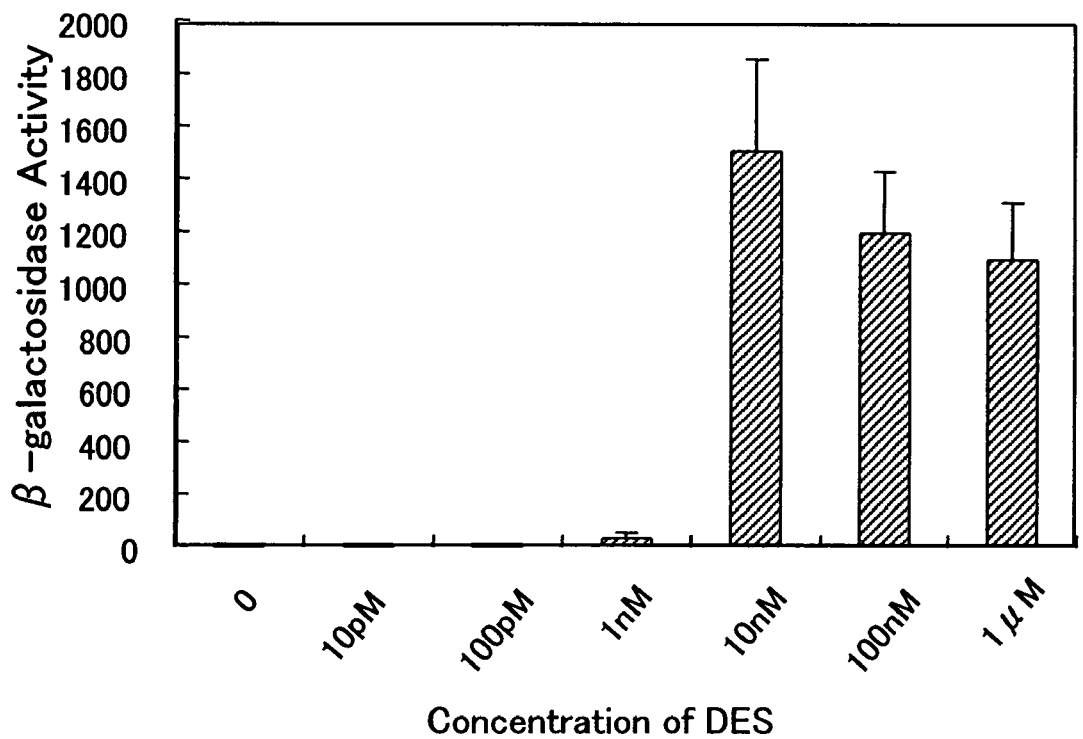
FIG. 8 is a diagram showing a result of measuring the ability of diethylstilbestrol (DES) to activate the estrogen receptor activity by the two-hybrid system using DNA enconding the ligand binding domain of the inventive receptor. The abscissa axis represents the concentration of DES in each experimental section. The left end column indicated by O corresponds to an experimental section in which DMSO was added at a final concentration of 0.1% in place of the DMSO solution of DES (DES-free section). The ordinate axis represents the β-galactosidase activity value, where the β-galactosidase activity value of the DES-free section is normalized as 1.
Figure 9:
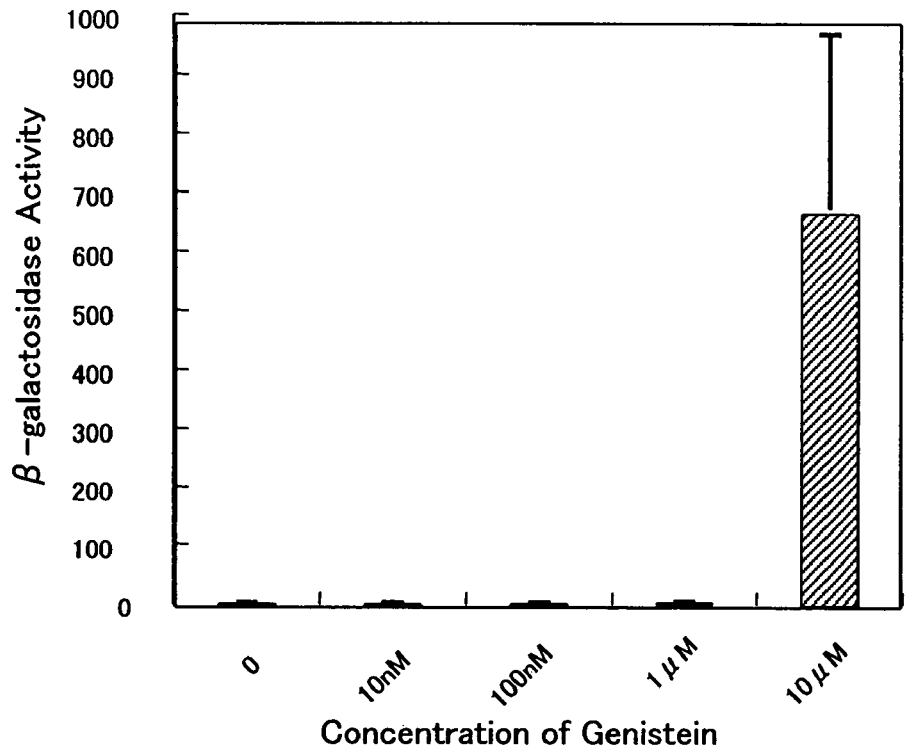
FIG. 9 is a diagram showing a result of measuring the ability of genistein to activate the estrogen receptor activity by the two-hybrid system using DNA encoding the ligand binding domain of the inventive receptor. The abscissa axis represents the concentration of genistein in each experimental section. The left end column indicated by O corresponds to an experimental section in which DMSO was added at a final concentration of 0.1% in place of the DMSO solution of genistein (genistein-free section). The ordinate axis represents the β-galactosidase activity value, where the β-galactosidase activity value of the genistein-free section is normalized as 1.
Figure 10:
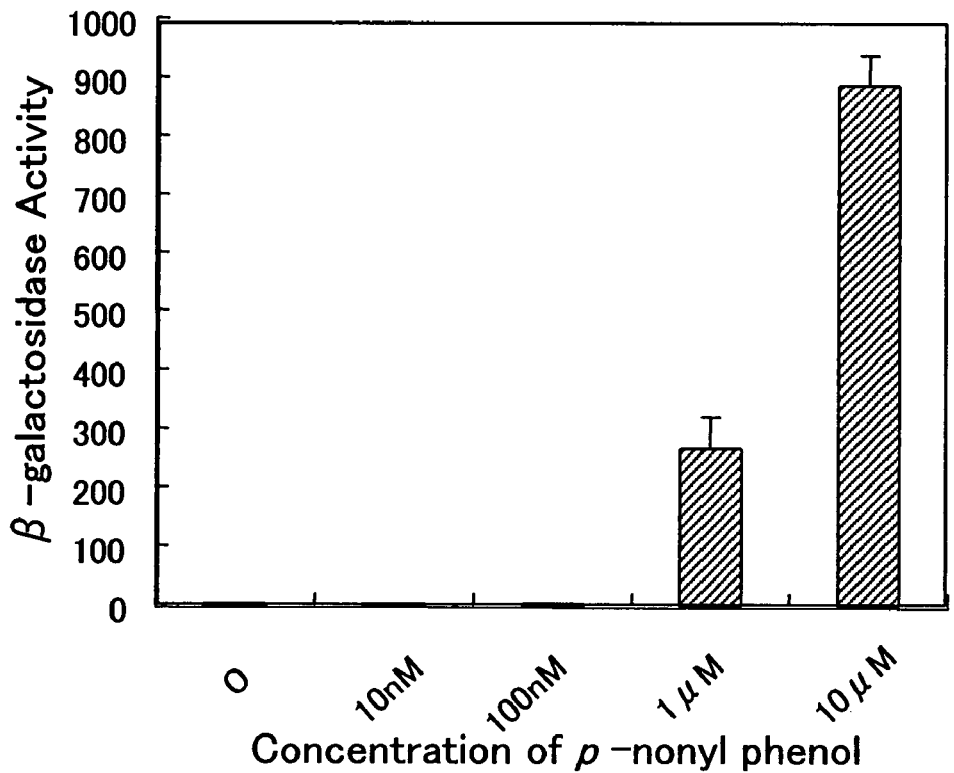
FIG. 10 is a diagram showing a result of measuring the ability of p-nonyl phenol to activate the estrogen receptor activity by the two-hybrid system using DNA encoding the ligand binding domain of the inventive receptor. The abscissa axis represents the concentration of p-nonyl phenol in each experimental section. The left end column indicated by O corresponds to an experimental section in which DMSO was added at a final concentration of 0.1% in place of the DMSO solution of p-nonyl phenol (p-nonyl phenol-free section). The ordinate axis represents the β-galactosidase activity value, where the β-galactosidase activity value of the p-nonyl phenol-free section is normalized as 1.

(4) Measuring the Ability of a Test Substance to Regulate Estrogen Receptor Activity Using the Yeast Two-hybrid System Part of yeast prepared in the example 4 (3) was inoculated in 1 ml of tryptophan and leucine-free SD medium, incubated at 30° C. all night while shaking, and the resultant culture solution was diluted to the absorbance at 595 nm of 0.015 with the tryptophan and leucine-free SD medium. On the 96-deep well plate, 250 µl of tryptophan and leucine-free SD medium was added, and 2.5 µl of various concentrations of E2 (manufactured by Wako Pure Chemical Industries, Ltd., final concentration of 1 pM to 10 µM), bisphenol A (manufactured by Wako Pure Chemical Industries, Ltd., final concentration of 10 nM to 10 µM), diethylstilbestrol (DES) (manufactured by Nacalai Tesque, Inc., final concentration of 10 pM to 10 µM), genistein (manufactured by Wako Pure Chemical Industries, Ltd., final concentration of 10 nM to 10 µM) or p-nonyl phenol (manufactured by Kanto Kagaku, final concentration of 10 nM to 10 µM), all of which were already dissolved with DMSO, was further added (final DMSO concentration of 1%). Furthermore, 10 µl of yeast cultured and diluted as described above was added on them, and they were incubated at 30° C. for four hours while shaking. After incubation, 10 µl of culture solution from each of the wells was collected, 100 µl of luminoreactive solution for β-galactositase activity measurement (Gal-Screen, manufactured by Tropix Corp.) was added on them, incubated at room temperature for approximate 1 hour, and the luminescence levels were measured using a luminometer LB96p (manufactured by BERTHOLD). The result of measuring the ability of the test substances to regulate estrogen receptor activity is shown in FIGS. 6 to 10.

Example 5

Preparing the Virus Particles and Virus Vector Containing the Inventive Gene

Two µg of DNA of the inventive vector pRc/RSVFMERα prepared in Example 2 is digested with 10 U of the restriction enzymes Spe I and XbaI at 37° C. for one hour, electrophoresis is performed on it using the low melting-point agarose gel, and approximately 1.8 kbp of DNA is collected. The DNA is treated using the DNA blunting kit (manufactured by Takara Shuzo Co., Ltd) to have blunt ends. On the other hand, 2 µg of pVL1392 vector DNA is digested with 10 U of restriction enzyme SmaI, treated with 10 U of alkaline phosphatase at 65° C. for one hour, electrophoresis was performed on it using the low melting-point agarose gel, and the DNA is collected. To 100 ng of pVL1392 vector DNA collected, approximately 100 ng of the 1.8 kbp DNA prepared from pRc/RSVFMERα as mentioned above is added and incubated with 5 U of T4 ligase at 16° C. for three hours. This is transduced into the *E. coli* DH5α strain competent cells (manufactured by TOYOBO CO., LTD.) in accordance with the supplied instructions, and the plasmid DNAs are prepared from the resultant colony by the alkaline method. Approximately 1 µg of plasmid DNAs are each digested with 10 U of restriction enzyme XbaI at 37° C. for one hour, electrophoresis is performed on it using Agarose S (manufactured by Nippon Gene Co., Ltd.) for analysis. The plasmid from which approximately 1.7 kbp of band would be detected is selected as transfer vectors pVL1392-FMERα.

To a 75 cm$^2$ T-flask (Falcon) are added 1×10$^6$ of Sf21 cells (available from ATCC), and cultured at 27° C. overnight using a Grace's medium containing 10% FBS and 2% Yeastlate (hereinafter referred to as the FBS-containing Grace medium). To 100 µl of the Grace's medium are added 10 µg of the transfer vector pVL1392-FMERα DNA and 20 ng of linearized viral genome DNA Baculo gold (Pharmingen). After 10 µl of lipofectin (GIBCO) 2-fold diluted with water is further added to the medium, the medium (the lipofectin-DNA mixture solution) is allowed to stand at room temperature for 30 minutes. After the overnight culture, the supernatant is removed from the Sf21 cell culture. The cells are washed with a small amount of a serum-free Grace's medium. To the cells is then added 5 ml of the same medium. The whole amount of the lipofectin-DNA mixture solution is then added to the cells, which is incubated 27° C. for 3 hours. The cells are then washed with the FBS-containing Grace medium. To the cells is also added 20 ml of the FBS-containing Grace medium, and the cells are cultured at 27° C. for 5 days. Day five of the culture, the supernatant is collected in a 50 ml centrifuge tube and centrifuged at 5000×g for 15 minutes to have cell debris precipitated, and then the centrifuged supernatant is collected. The whole amount of the collected supernatant is centrifuged at 100,000×g for 24 hours to give precipitated viral particles that contain the inventive gene. The precipitate is suspended in 100 µl of TE. An equivalent amount of TE-saturated phenol is added thereto and gently mixed at room temperature for 24 hours. After the mixture is centrifuged at 10,000×g for 10 minutes, a water layer is collected. An equivalent amount of chloroform is added to the collected water layer and gently mixed for 10 minutes. The mixture is again centrifuged at 10,000×g for 10 minutes, and then the water layer is collected. To the collected water layer are added NaCl at a final concentration of 0.2 M and a 2.5-fold amount of ethanol, and a viral vector DNA that contains the inventive gene is precipitated and collected.

Example 6

Preparing the Transformant in Which the Virus Vector Containing the Inventive Gene was Transduced into Sf21 Cell and Manufacturing the Inventive Receptor To each of ten 75 cm$^2$ T-flasks (Falcon) is added 1×10$^6$ of Sf21 cells (available from ATCC), and cultured in the FBS-containing Grace medium at 27° C. In each flask, 10 µl/flask of the culture supernatant, which is prepared in Example 5 and contains the inventive gene-containing viral particles, is added to the cells, which are cultured in situ for 4 days. The culture supernatant is harvested from each flask and then added to Sf21 cells, which are similarly cultured in each of ten 75 cm$^2$ T-flasks (Falcon), in an amount of 1 ml per flask. The cells are cultured for 60 hours in each flask and then suspended by pipetting and harvested from each flask. The resulting cell suspension is centrifuged at 5,000×g for 15 minutes to have the cells precipitated. The precipitate is suspended in a buffer comprising 20 mM HEPES pH 7, 1 mM EDTA, 1 mM DTT, and 0.5 mM PMSF, and then the suspension is homogenized with 30 up-and-down strokes in a Dounce homogenizer to form a cell homogenate. The homogenate is centrifuged at 30,000×g for 1 hour, and the supernatant fraction is collected to give a fraction that contains the inventive receptor.

Example 7

Receptor Binding Assay Using the Inventive Receptor

A binding reaction buffer is prepared to have a final composition of 20 mM HEPES-KOH pH 7.9, 10 mM sodium molybdate, 1 mM DTT, 0.5 mM EDTA, and 0.5 mM PMSF. The reaction solution has a total volume of 100 µl. To the binding reaction buffer are added a 10 µg protein equivalent of the inventive receptor-containing fraction prepared in Example 6 and tritium-labeled E2 at a content of 1 pM to 100 nM. In the group for determining nonspecific binding, unlabeled E2 is further added at a final concentration of 10 µM to form a reaction solution.

The binding reaction is carried out as follows. After the reaction solution is held on ice for 15 hours, 100 µl of a charcoal dextran liquid (composition: 10 mM Tris-HCl, 0.2% acid-washed active carbon (NoritA, Nacalai Tesque), and 0.005% Pharmacia Dextran T70) is added, and the reaction mixture is allowed to stand on ice for 10 minutes. The reaction mixture is centrifuged at 1,000×g for 10 minutes in a low-speed centrifuge to have the active carbon precipitated, and then 100 µl of the supernatant is sampled. The radioactivity of the sampled supernatant is measured using a liquid scintillation counter. Based on the measured value, the amount of the labeled E2 in the supernatant is determined, which corresponds to the amount of the labeled E2 bound to the estrogen receptor (the amount of the bound form of the labeled ligand). In the experimental section to which only the labeled E2 is added, the amount of the bound form of the labeled ligand corresponds to the total amount of the labeled E2 bound to the estrogen receptor (the total binding amount). In the experimental section to which the labeled E2 and unlabeled E2 are added, the amount of the bound form of the labeled ligand corresponds to the amount of the labeled E2 nonspecifically bound to the receptor (the nonspecific binding amount). As for each of the experimental sections to which the labeled E2 is added at different concentrations, respectively, the nonspecific binding amount is subtracted from the total binding amount to produce the amount of the labeled ligand specifically bound to the estrogen receptor (the specific binding amount) in each group. Thereafter, the value of (the concentration of the labeled ligand specifically bound)/(the concentration of the free form of the labeled ligand) is plotted against the Y-axis, and the concentration of the labeled ligand specifically bound is plotted against the X-axis. The Scatchard analysis is performed to produce a Kd value of the inventive receptor with respect to E2.

In order to determine the affinity of a test substance for the inventive receptor, the test substance is added at a final concentration of about 1% to the binding assay reaction solution, which contains about 1 nM of the labeled E2 similarly to the above. In the test substance-free experimental section, the same amount of solvent is added to the reaction solution in place of the test substance. When the addition of the test substance reduces the amount of the labeled E2 bound to the estrogen receptor, the test substance is determined as an estrogen receptor binding substance.

INDUSTRIAL APPLICABILITY

According to the present invention, the novel estrogen receptor gene and the like can be applied to assay systems for evaluating the ability of chemical substances to regulate the estrogen receptor activity.

Free Text in Sequence Listing

SEQ ID NO:4
Designed oligonucleotide primer for PCR

SEQ ID NO:5
Designed oligonucleotide primer for PCR

SEQ ID NO:6
Designed oligonucleotide primer for PCR

SEQ ID NO:7
Designed oligonucleotide primer for PCR

SEQ ID NO:8
Designed oligonucleotide primer for PCR

SEQ ID NO:9
Designed oligonucleotide primer for PCR

SEQ ID NO:10
Designed oligonucleotide to synthesize promoter DNA

SEQ ID NO:11
Designed oligonucleotide to synthesize promoter DNA

SEQ ID NO:12
Designed oligonucleotide primer for PCR

SEQ ID NO:13
Designed oligonucleotide primer for PCR

SEQ ID NO:14
Designed oligonucleotide primer for PCR

SEQ ID NO:15
Designed oligonucleotide primer for PCR

---

What is claimed is:

1. An isolated estrogen receptor gene coding for any of the following estrogen receptors (a) to (c):
   (a) an estrogen receptor comprising the amino acid sequence represented by amino acid numbers 153 to 602 in the amino acid sequence of SEQ ID NO: 1,
   (b) an estrogen receptor comprising the amino acid sequence of SEQ ID NO: 1, and
   (c) an estrogen receptor comprising an amino acid sequence exhibiting 95% or more amino acid identity to the amino acid sequence represented by amino acid numbers 153 to 602 in the amino acid sequence of SEQ ID NO: 1.

2. An isolated estrogen receptor gene comprising any of the following nucleotide sequences (d) to (e):
   (d) the nucleotide sequence represented by nucleotide numbers 460 to 1809 in the nucleotide sequence of SEQ ID NO: 2, and
   (e) the nucleotide sequence represented by nucleotide numbers 4 to 1809 in the nucleotide sequence of SEQ ID NO: 2.

3. A vector comprising the estrogen receptor gene according to claim 1.

4. The vector according to claim 3, wherein a promoter is operably linked to the estrogen receptor gene.

5. The vector according to claim 3, wherein the vector is a virus.

6. A viral particle containing the estrogen receptor gene according to claim 1.

7. A method for producing a vector, comprising incorporating the estrogen receptor gene according to claim 1 into a vector replicable in a host cell.

8. A transformant, wherein the estrogen receptor gene according to claim 1 is introduced into an isolated or nonhuman host cell.

9. The transformant according to claim 8, wherein the estrogen receptor gene is introduced into a chromosome of the host cell.

10. The transformant according to claim 8, wherein the host cell is an animal cell.

11. The transformant according to claim 8, wherein the host cell is a mammalian cell.

12. The transformant according to claim 8, wherein the host cell is an insect cell.

13. The transformant according to claim 8, wherein the host cell is a yeast cell.

14. A method for producing a transformant, comprising introducing the estrogen receptor gene according to claim 1 into a host cell, thereby producing the transformant.

15. A method for manufacturing an estrogen receptor, comprising culturing the transformant according to claim 8, thereby producing the estrogen receptor.

16. A DNA consisting of a nucleotide sequence of 300 or more nucleotides of the estrogen receptor gene according to claim 1.

17. The DNA according to claim 16, wherein nucleotide sequence is a nucleotide sequence coding for the ligand binding domain of the estrogen receptor.

* * * * *